(12) United States Patent
Goldberg et al.

(10) Patent No.: US 6,498,144 B1
(45) Date of Patent: *Dec. 24, 2002

(54) USE OF SCATTER FACTOR TO ENHANCE ANGIOGENESIS

(75) Inventors: Itzhak D. Goldberg, Englewood, NJ (US); Eliot M. Rosen, Port Washington, NY (US)

(73) Assignee: North Shore - Long Island Jewish Research Institute, Manhasset, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/602,302

(22) Filed: Jun. 23, 2000

Related U.S. Application Data

(63) Continuation of application No. 09/048,813, filed on Mar. 26, 1998, which is a continuation-in-part of application No. 08/746,636, filed on Nov. 13, 1996, now Pat. No. 5,837,676, which is a continuation of application No. 08/138,667, filed on Oct. 18, 1993, now abandoned.

(51) Int. Cl.[7] .............................................. A61K 38/00
(52) U.S. Cl. ............................. 514/12; 514/2; 530/324; 530/350; 530/399
(58) Field of Search ........................ 514/2, 12; 530/324, 530/426, 399

(56) References Cited

U.S. PATENT DOCUMENTS 5,837,676 A * 11/1998 Goldberg et al.
5,919,759 A *  7/1999 Goldberg et al.
5,965,523 A * 10/1999 Goldberg et al.

OTHER PUBLICATIONS

Grant et al. Scatter Factor induces blood vessel formation in vivo. (Mar. 1993) Proc. Natl. Aad. Sci USA vol. 90, pp.1937–1941.*

Pu et al. Enhanced revascularization of the ishemic limb by angiogenic therapy. (Jul. 1993) Circulation vol. 88 (1), pp.208–218 (abstract only).*

* cited by examiner

Primary Examiner—Gary L. Kunz
Assistant Examiner—Pamela Holbrook
(74) Attorney, Agent, or Firm—Amster, Rothstein & Ebenstein

(57) ABSTRACT

This invention relates to a method of enhancing wound healing and to a method of enhancing organ transplantation utilizing scatter factor, either alone or in combination with a growth factor.

5 Claims, 12 Drawing Sheets

Control       SF (20 ng)

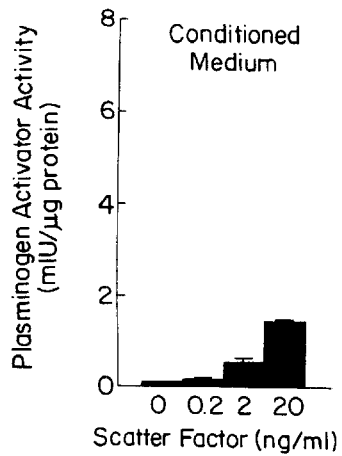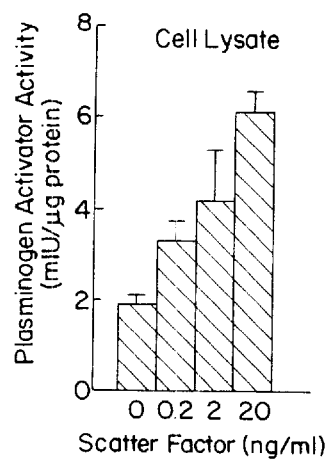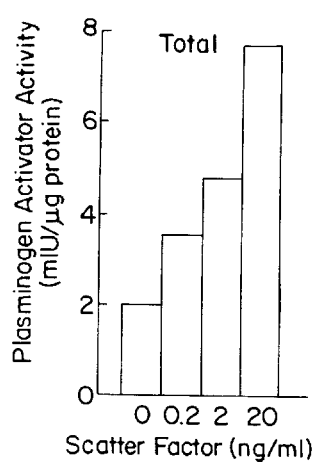
FIG. 4A   FIG. 4B   FIG. 4C
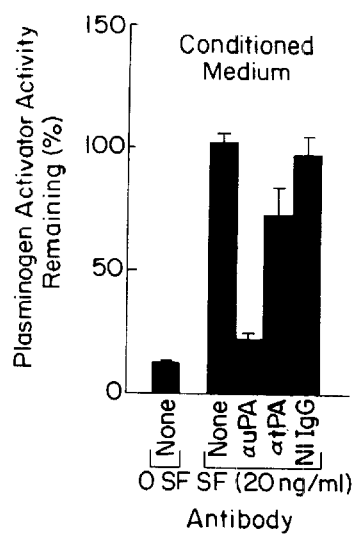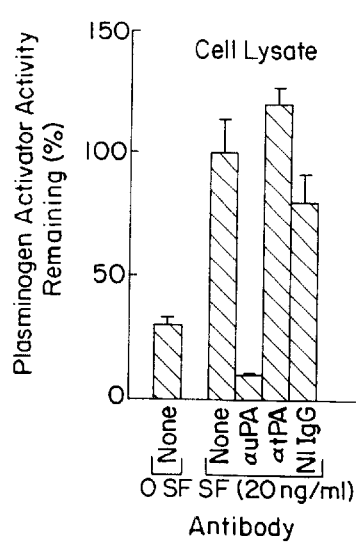
FIG. 4D   FIG. 4E 1 2 3 4 5 6    7 8

28S →

18S →

21 29 34

1 2 3 4

SF → c-met →

β-actin →

USE OF SCATTER FACTOR TO ENHANCE ANGIOGENESIS

CROSS REFERENCE TO RELATED APPLICATIONS

This application is a continuation of U.S. patent application Ser. No. 09/048,813, filed Mar. 26, 1998, which is a continuation-in-part of co-pending U.S. patent application Ser. No.08/746,636, filed Nov. 13, 1996, now U.S. Pat. No. 5,837,676, which is a continuation of U.S. patent application Ser. No. 08/138,667, filed Oct. 18, 1993, now abandoned, the contents of each of which are hereby incorporated by reference in their entirety.

STATEMENT OF GOVERNMENT INTEREST

This invention was made with government support under NIH Grant No. CA50516. As such, the government has certain rights in the invention.

FIELD OF THE INVENTION

This invention relates to a method of enhancing wound healing and to a method of enhancing organ transplantation comprising the administration of scatter factor to promote angiogenesis.

BACKGROUND OF THE INVENTION

Scatter factor has previously been described as a cytokine which is secreted by fibroblasts (see Stoker et al., *J. Cell Sci.*, Vol. 77, pp. 209–223 (1985) and Stoker et al., *Nature* (London), Vol. 327, pp. 238–242 (1987)) and by vascular smooth muscle cells (see Rosen et al., In Vitro *Cell Dev. Biol.*, Vol. 25, pp. 163–173 (1989)). Scatter factor has been shown to disperse cohesive epithelial colonies and stimulate cell motility. In addition, scatter factor has been shown to be identical to hepatocyte growth factor (HGF) (see Weidner et al., *Proc. Nat'l. Acad. Sci. USA*, Vol. 88, pp. 7001–7005 (1991) and Bhargava et al., *Cell Growth Differ.*, Vol. 3, pp. 11–20 (1992)), which is an independently characterized serum mitogen (see Miyazawa et al., *Biochem. Biophys. Res. Commun.*, Vol. 169, pp. 967–973 (1989) and Nakamura et al., *Nature* (London), Vol. 342, pp. 440–443 (1989)). Scatter factor induces kidney epithelial cells in a collagen matrix to form branching networks of tubules, suggesting that it can also act as a morphogen (see Montesano et al., *Cell*, Vol. 67, pp. 901–908 (1991)).

Scatter factor (HGF) is a basic heparin-binding glycoprotein consisting of a heavy (58 kDa) and a light (31 kDa) subunit. It has 38% amino acid sequence identity with the proenzyme plasminogen (see Nakamura et al., *Nature* (London), Vol. 342, pp. 440–443 (1989)) and is thus related to the blood coagulation family of proteases. Its receptor in epithelium has been identified as the c-met protooncogene product, a transmembrane tyrosine kinase (see Bottaro et al., *Science*, Vol. 251, pp. 802–804 (1991) and Naldini et al., *Oncogene*, Vol. 6, pp. 501–504 (1991)).

Scatter factor has been found to stimulate endothelial chemotactic and random migration in Boyden chambers (see Rosen et al., *Proc. Soc. Exp. Biol. Med.*, Vol. 195, pp. 34–43 (1990)); migration from carrier beads to flat surfaces (see Rosen et al., *Proc. Soc. Exp. Biol. Med.*, Vol. 195, pp. 34–43 (1990)); formation of capillary-like tubes (see Rosen et al., *Cell Motility Factors*, (Birkhauser, Basel) pp. 76–88 (1991)) and DNA synthesis (see Rubin et al., *Proc. Nat'l. Acad. Sci. USA*, Vol. 88, pp. 415–419 (1991)). In addition, preliminary studies have suggested that scatter factor induces endothelial secretion of plasminogen activators (see Rosen et al., *Cell Motility Factors*, (Birkhauser, Basel) pp. 76–88 (1991)).

The term "angiogenesis", as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., *Adv. Cancer Res.*, Vol. 43, pp. 175–203 (1985)). These processes are controlled by soluble factors and by the extracellular matrix (see Ingber et al., *Cell*, Vol. 58, pp. 803–805 (1985)).

Because proteases, such as plasminogen activators (the endothelial secretion of which is induced by scatter factor) are required during the early stages of angiogenesis, and since endothelial cell migration, proliferation and capillary tube formation occur during angiogenesis, the inventors hypothesized that scatter factor might enhance angiogenic activity in vivo. In addition, it is desirable to enhance angiogenic activity so that wound healing and organ transplantation can be enhanced.

It is therefore an object of this invention to provide method of enhancing angiogenic activity.

It is a further object of this invention to provide a method of enhancing wound healing.

It is a still further object of this invention to provide a method of enhancing organ transplantation.

SUMMARY OF THE INVENTION

This invention is directed to a method of promoting angiogenesis by administration of scatter factor. The promotion of angiogenesis can be used for promoting wound healing and treating various conditions where the promotion of angiogenesis is desirable, including, but not limited to, ischemia

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawing wherein:

FIG. 1 is comprised of FIG. 1A, FIG. 1B, FIG. 1C and FIG. 1D. FIG. 1 represents the result of a murine angiogenesis assay.

FIG. 2 is comprised of FIG. 2A, FIG. 2B, FIG. 2C and FIG. 2D. FIG. 2 represents the microscopic appearance of Matrigel plugs.

FIG. 3 is comprised of FIG. 3A, FIG. 3B, FIG. 3C, FIG. 3D and FIG. 3E. FIG. 3 represents scatter factor-induced angiogenesis in rat corneas.

FIG. 4 is comprised of FIG. 4A, FIG. 4B, FIG. 4C, FIG. 4D and FIG. 4E. FIG. 4 represents stimulation of plasminogen activator expression by scatter factor. FIG. 4A shows secreted activity during a 6 hour collection interval. FIG. 4B shows secreted activity intracellularly. FIG. 4C shows total (secreted plus intracellular) activity. FIG. 4D and FIG. 4E show plasminogen activator activity in medium and in lysates from cells treated with scatter factor at 20 ng/ml assayed in the presence of goat anti-human urokinase IgG (auPA), goat anti-human tissue type PA IgG (atPA) or goat nonimmune IgG (NI IgG) (200 mg/ml), respectively.

FIG. 5 is comprised of FIG. 5A, FIG. 5B, FIG. 5C and FIG. 5D. FIG. 5 represents the results of immunohistochemical staining of skin biopsy samples for scatter factor.

FIG. 6A: Western blotting. One-hundred µl aliquots of concentrated conditioned media (see Materials and Methods) were electrophoresed on a 12% non-reduced SDS-polyacrylamide gel and blotted to detect SF. Lanes 1–4 represent media from (SF+neo) transfected clones 21, 29, 52, and 3–7, respectively; lanes 5 and 6 represent media from neo-only transfected clones 32 and 34; and lanes 7 and 8 represent positive standards [native human placental SF and rhSF (50 ng)]. FIG. 6B. Northern blotting. Total cell RNA was isolated from two SF-transfected clones (21 and 29) and one control (neo) clone (34). Equal aliquots of RNA (30 µg/lane) were electrophoresed, and blots were prepared. Blots were probed using a 500 bp SF cDNA probe labeled with digoxigenin and developed using anti-digoxigenin antibody. Bands of the expected size [slightly larger than full-length SF cDNA (2.3 kb)] were observed for clones 21 and 29, whereas no bands were detected for clone 34.

FIGS. 9A and 9B show results from two separate experiments (Experiments 3 and 2, respectively). Comparisons of pooled data for SF+ clones (21+29) vs SF− clones (32+34) were made at each time point using two-tailed t-tests. Significant comparisons are shown in the figure (* indicates P<0.05; ** indicates P<0.01). In addition, in FIG. 9A, comparisons of clone 21 vs pooled clones (32+34) were significant at P<0.01 for all time points (wks 1–9); and comparisons of clone 29 vs pooled clones (32+34) were significant at P<0.01 for wks 7–9.

FIG. 10A: Stimulation of HDMEC chemotaxis by SF and its inhibition by anti-SF monoclonal AB. rhSF was tested for chemotactic activity alone or in the presence of anti-SF monoclonal MO294 (AB) at 2 or 20 µg/ml (following a 30 min pre-incubation with AB). Values plotted are means±SEMs of three assays. FIGS. 5B and 5C: Assays of conditioned media (CM) from SF+ vs SF− cell clones. In FIG. 10B, CM was concentrated 10-fold using a 10 kDa membrane and assayed for chemotactic activity at three different protein concentrations. Values plotted are means of triplicate assays. SEMs were<5% of the mean values. In FIG. 10C, CM (50 µg/ml) was pre-incubated without or with anti-SF monoclonal AB (20 µg/ml) for 30 min and assayed for chemotactic activity. Migration values are expressed as a percentage of the control (no CM, no AB) and represent means±SEMs of triplicate assays. * indicates significant inhibition of migration by AB (P<0.001). FIGS. 10D and 10E: Assays of extracts of primary tumors derived from SF+ vs SF− clones. In FIG. 10D, tumor extracts were tested for chemotactic activity at three different protein concentrations. For each clone, two different extracts were tested, and each extract was assayed in triplicate. Migration values for the two extracts from the same clone were nearly identical, and these values were averaged. Thus, each value plotted is a mean of six assays per clone, with SEMs<5% of means. In FIG. 10E, extracts from clones 21 and 29 (50 µg/ml) were pre-incubated without or with anti-SF monoclonal AB (20 µg/ml) for 30 min and assayed for chemotactic activity. Values are expressed as a percentage of the control (no extract, no AB) and represent means±SEMs of triplicate assays. * indicates significant inhibition of migration by AB (P<0.01).

FIG. 11A shows a negative neovascular response 7 days after implanting a Hydron pellet containing buffered saline. FIG. 11B shows a positive neovascular response induced by 50 ng of human recombinant SF. Note the directional ingrowth of capillaries toward the Hydron implant located at the center of the photograph. [The dose of 50 ng of SF gives a strong but sub-maximal angiogenic response; SF doses of 100 ng or more give maximal responses (Grant et al., 1993).] A vigorous neovascular response was induced by 5 µg of extract from a SF+ clone 21 tumor (FIG. 11C). A positive but substantially weaker neovascular response was induced by 5 µg of SF− clone 32 tumor extract (FIG. 11D). FIG. 11E shows a markedly attenuated neovascular response induced by 5 µg of SF+ clone 21 tumor extract in the presence of 2.5 µg of anti-SF neutralizing monoclonal antibody MO294.

DETAILED DESCRIPTION OF THE INVENTION

Figure 1A:
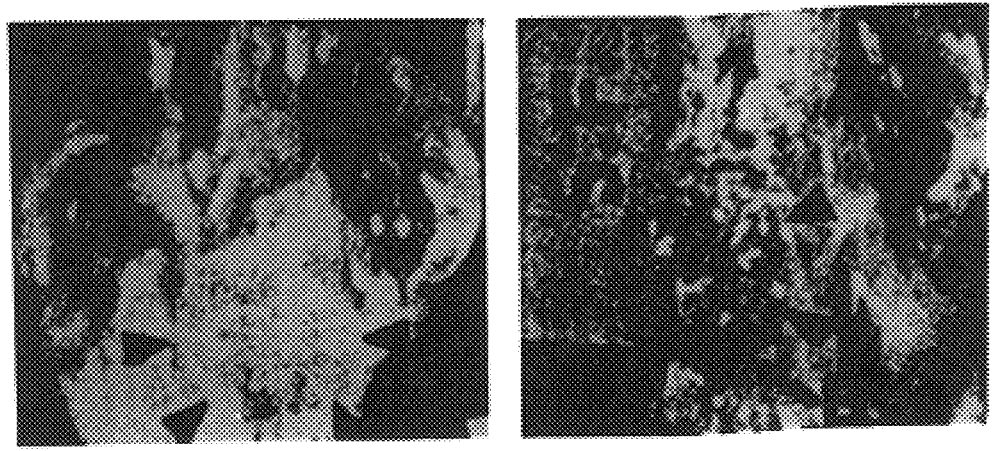
FIG. 1A shows Matrigel plugs (arrowheads) before excision of the plugs.

The present invention is directed to a method of promoting angiogenesis in a tissue or subject by 10 administering scatter factor to a subject in need of angiogenesis promotion. Specifically, the method provided by the present invention involves the administration of scatter factor to promote angiogenesis in various tissues to promote wound healing, The administration of scatter factor may be effected by administration of the protein itself or administration of a nucleic acid encoding scatter factor by the use of standard DNA techniques.

Scatter factor protein may be administered to a tissue or subject topically or by intravenous, intramuscular, intradermal, subcutaneous or intraperitoneal injection. Scatter factor protein is administered in amounts sufficient to promote angiogenesis in a subject, which is in the amount of about 0.1–1000 ng/kg body weight.

Scatter factor protein may be administered as the wild type scatter factor protein, or analogues thereof, and may be produced synthetically or recombinantly, or may be isolated from native cells. As used herein, "analogue" means functional variants of the wild type protein, and includes scatter factor protein isolated from mammalian sources other than human, such as mouse, as well as functional variants thereof.

A nucleic acid sequence encoding scatter factor administered to a mammal may be genomic DNA or cDNA. The nucleic acid sequence may be administered using a number of procedures known to one skilled in the art, such as electroporation, DEAE Dextran, monocationic liposome fusion, polycationic liposome fusion, protoplast fusion, DNA coated microprojectile bombardment, by creation of an in vivo electrical field, injection with recombinant replication-defective viruses, homologous recombination, and naked DNA transfer. It is to be appreciated by one skilled in the art that any of the above methods of DNA transfer may be combined.

A nucleic acid encoding scatter factor may also be administered to a mammal using gene therapy, i.e. by the administration of a recombinant vector containing a nucleic acid sequence encoding scatter factor. The nucleic acid sequence may be, for example, genomic DNA or cDNA. The recombinant vector containing nucleic acid encoding scatter factor may be administered to a mammal using any number of procedures known to one skilled in the art, including, but not limited to, electroporation, DEAE Dextran transfection, calcium phosphate transfection, cationic liposome fusion, protoplast fusion, by creation of an in vivo electrical field, DNA coated microprojectile bombardment, injection with recombinant replication-defective viruses, homologous recombinantion, gene therapy, and naked DNA transfer. It is to be appreciated by one skilled in the art that any of the above methods of nucleic acid transfer may be combined. Accordingly, a cell, such as a stem cell or a tumor cell which expresses scatter factor introduced therein through viral transduction, homologous recombination, or transfection is also provided by the present invention. This cell may then be administered to a subject to promote angiogenesis..

The recombinant vector may comprise a nucleic acid of or corresponding to at least a portion of the genome of a virus, where this portion is capable of directing the expression of a nucleic sequence encoding scatter factor, operably linked to the viral nucleic acid and capable of being expressed as a functional gene product in the subject mammal. The recombinant vectors may be derived from a variety of viral nucleic acids known to one skilled in the art, e.g. the genomes of HSV, adenovirus, adeno-associated virus, Semiliki Forest virus, vaccinia virus, and other viruses, including RNA and DNA viruses.

The recombinant vectors may also contain a nucleotide sequence encoding suitable regulatory elements so as to effect expression of the vector construct in a suitable host cell. As used herein, "expression" refers to the ability of the vector to transcribe the inserted DNA sequence into mRNA so that synthesis of the protein encoded by the inserted nucleic acid can occur. Those skilled in the art will appreciate that a variety of enhancers and promoters are suitable for use in the constructs of the invention, and that the constructs will contain the necessary start, termination, and control sequences for proper transcription and processing of the nucleic acid sequence encoding scatter factor when the recombinant vector construct is introduced into a mammal.

Vectors suitable for the expression of the nucleic sequence encoding scatter factor are well known to one skilled in the art and include pMEX, pRSX24 (provided by Dr. George Vande Woude, Frederick Cancer Center, Frederick, Md.), pSV2neo (Clonetech), pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pVl1392 (Invitrogen), pCDM8 (Invitrogen), pcDNA I (Invitrogen), pcDNA I(amp) (Invitrogen), pZeoSV (Invitrogen), pcDNA 3 (Invitrogen), pRc/CMV (Invitrogen), pRc/RSV (Invitrogen) pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

Suitable promoters include, but are not limited to, constitutive promoters, tissue specific promoters, and inducible promoters. Expression of the nucleic acid sequence encoding scatter factor may be controlled and affected by the particular vector into which the nucleic acid sequence has been introduced. Some eukaryotic vectors have been engineered so that they are capable of expressing inserted nucleic acids to high levels within the target cell. Such vectors utilize one of a number of powerful promoters to direct the high level of expression. Eukaryotic vectors use promoter-enhancer sequences of viral genes, especially those of tumor viruses. A particular embodiment of the invention provides for regulation of expression of the nucleic acid sequence encoding scatter factor using inducible promoters. Non-limiting examples of inducible promoters include, but are not limited to, metallothionine promoters and mouse mammary tumor virus promoters. Depending on the vector, expression of the nucleic acid sequence encoding scatter factor would be induced in the mammal by the addition of a specific compound at a certain point in the growth cycle of the cells of the mammal. Other examples of promoters and enhancers effective for use in the recombinant vectors include, but are not limited to, CMV (cytomegalovirus), SV40 (simian virus 40), HSV (herpes simplex virus), EBV (epstein-barr virus), retroviral, adenoviral promoters and enhancers, and tumor cell specific promoters and enhancers.

It is within the confines of the invention that scatter factor may be administered in combination with a growth factor to promote angiogenesis, including, but not limited to TGF-α, FGF and PDGF.

Scatter factor, in the form of a protein, nucleic acid, or a recombinant vector containing nucleic acid encoding scatter factor, may be administered to a subject prior to, simultaneously with or subsequent to administration of a growth factor.

For the purposes of gene transfer into a tissue or subject, a recombinant vector containing nucleic acid encoding scatter factor may be combined with a sterile aqueous solution which is preferably isotonic with the blood of the recipient. Such formulations may be prepared by suspending the recombinant vector in water containing physiologically compatible substances such as sodium chloride, glycine, and the like, and having buffered pH compatible with physiological conditions to produce an aqueous solution, and rendering such solution sterile. In a preferred embodiment of the invention, the recombinant vector is combined with a 20–25% sucrose in saline solution in preparation for introduction into a mammal.

The amounts of nucleic acid encoding scatter factor, or nucleic acid encoding scatter factor contained in a vector are administered in amounts sufficient to promote angiogenesis in a subject. However, the exact dosage will depend on such factors as the purpose of administration, the mode of administration, and the efficacy of the composition, as well as the individual pharmacokinetic parameters of the subject. Such therapies may be administered as often as necessary and for the period of time as judged necessary by one of skill in the art.

Non-limiting examples of tissues into which nucleic acid encoding scatter factor may be introduced to promote angiogenesis include fibrous, endothelial, epithelial, vesicular, cardiac, cerebrovascular, muscular, vascular, transplanted, and wounded tissues.

Transplanted tissues are, for example, heart, kidney, lung, liver and ocular tissues.

The tissues into which nucleic acid encoding scatter factor may be introduced to promote angiogenesis include those associated with diseases or conditions selected from the group consisting of ischemia, circulatory disorders, vascular disorders, myocardial ischemic disorders, myocardial disease, pericardial disease or congenital heart disease. Non-limiting examples of ischemia are myocardial ischemia, cerebrovascular ischemia and veno-occlusive disorder. An example of myocardial ischemia is coronary artery disease.

In further embodiments of the invention, scatter factor is used to enhance wound healing, organ regeneration, and organ transplantation, including the transplantation of artificial organs. In addition, scatter factor can be used to accelerate endothelial cell coverage of vascular grafts in order to prevent graft failure due to reocclusion, and to enhance skin grafting. Further, antibodies to scatter factor can be used to treat tumors and to prevent tumor growth.

The present invention is described in the following Examples which are set forth to aid in the understanding of the invention, and should not be construed to limit in any way the scope of the invention as defined in the claims which follow thereafter.

EXAMPLE I

Scatter Factor Preparations. In order to prepare scatter factor preparations, mouse scatter factor was purified from serum-free culture medium from ras-transformed NIH/23T3 cells (clone D4) by cation-exchange chromatography as described by Rosen et al., *Proc. Soc. Exp. Biol. Med.*, Vol. 195, pp. 34–43 (1990), followed by immunoaffinity chromatography and ultrafiltration. Recombinant human HGF (rhHGF) was provided by Toshikazu Nakamura (Kyushu University, Fukuoka, Japan). Scatter factor (HGF) is commercially available from Collaborative Research, Bedford, Mass.

Antibody Preparations. In order to make the antibody preparations, antisera to native human placental scatter factor and rhHGF were prepared by immunizing rabbits with purified factors (see Bhargava et al., *Cell Growth Differ.*, Vol. 3, pp. 11–20 (1992) and Bhargava et al., *Cell Motility Factors*, (Birkhauser, Basel) pp. 63–75 (1991)). A chicken egg yolk antibody to human placental scatter factor was prepared by immunizing two White Leghorn hens, 22–24 weeks old, with 500 mg of human placental scatter factor emulsified in complete Freund's adjuvant. Booster injections were given 14 to 28 days later, and the eggs were collected daily. The IgG fraction from seven eggs was extracted and partially purified by the methods described by Polson et al., *Immunol. Commun.*, Vol. 9, pp. 495–514 (1980). The final preparation contained 80 mg of protein per ml in phosphate-buffered saline (PBS). Antibody specificity was established by recognition of mouse and human scatter factors on immunoblots, specific binding of scatter factor to antibody-Sepharose columns, and inhibition of the in vitro biologic activities of mouse and human scatter factor.

Plasminogen Activator Assays. In order to perform plasminogen activator assays, bovine brain microvessel endothelial cells (BBEC) were isolated from brain cortex after removal of the pia mater, identified as endothelial, and cultured by standard techniques. BBEC (passage 10–12) at about 80% confluency in 60 mm Petri dishes were treated with mouse scatter factor for 24 hours, washed, and incubated for 6 hours in 2.5 ml of serum-free Dulbecco's modified Eagle's medium (DMEM) to collect secreted proteins. The cells were washed, scraped into PBS, collected in 0.5 ml of PBS by centrifugation, and lysed by sonication. Aliquots of medium and cell lysates were assayed for PA activity by a two-step chromogenic reaction as described by Coleman et al., *Ann. N.Y. Acad. Sci.*, Vol. 370, pp. 617–626 (1991). Human high molecular weight urokinase (American Diagnostica, Greenwich, Conn.) was used as the standard. The protein content of the lysate was determined by using the Bradford dye-binding assay (Bio-Rad).

Murine Angiogenesis Assays. In order to perform the murine angiogenesis assay, angiogenesis was assayed as growth of blood vessels from subcutaneous tissue into a solid gel of basement membrane containing the test sample. Matrigel (7 mg in 0.5 ml; Collaborative Research) in liquid form at 4° C. was mixed with scatter factor and injected into the abdominal subcutaneous tissues of athymic XID nude beige mice or C57BL/6 mice. Matrigel rapidly forms a solid gel at body temperature, trapping the factor to allow slow release and prolonged exposure to surrounding tissues. After 10 days, the mice were sacrificed and the Matrigel plugs were excised and fixed in 4% formaldehyde in phosphate buffer. Plugs were embedded in paraffin, sectioned, stained with Masson's trichrome (which stains endothelial cells reddish-purple and stains the Matrigel violet or pale green), and examined for ingrowth of blood vessels. Vessel formation was quantitated from stained sections using the Optimax digital image analyzer connected to an Olympus microscope (see Grant et al., *Cell*, Vol. 58, pp. 933–943 (1989)). Results were expressed as mean vessel area per field±SEM (arbitrary units) or as total vessel area ($mm^2$) in 20 random fields.

Rat Cornea Angiogenesis Assays. In order to perform the rat cornea angiogenesis assay, angiogenesis was assayed in the avascular rate cornea, as described by Polverini et al., *Lab. Invest.*, vol. 51, pp. 635–642 (1984). Test samples were combined 1:1 with a sterile solution of Hydron (Interferon Laboratories, New Brunswick, N.J.) and air-dried overnight. A 5 ml pellet was inserted into a surgically created pocket in the corneal stroma and positioned 1–1.5 mm from the limbus. Corneas were examined daily with a dissecting microscope for up to 7 days for capillary growth. Assay responses were scored as positive if sustained directional ingrowth of capillary sprouts and hairpin loops occurred during the observation period. Responses were scored as negative either when no neovascularization was detected or when only an occasional sprout or hairpin loop was observed that showed no evidence of sustained directional ingrowth. After 7 days, corneas were perfused with colloidal carbon, and whole-mount preparations were examined and photographed.

Immunohistochemistry. To study immunohistochemistry, five-micrometer-thick cryostat sections were prepared from biopsy samples of plaques or of areas of normal skin in patients with active psoriasis. The sections were stained by using an avidin-biotin immunoperoxidase technique (see Griffiths et al., *Am. Acad. Dermatol.*, Vol. 20, pp. 617–629 (1989)). The chromogen was Texas red conjugated to avidin. The primary antibody was rabbit polyclonal antiserum to purified native human placental scatter factor or to rhHGF (1:1000 dilution). Nonimmune rabbit serum (1:1000) was used as a negative control.

Figure 1B:
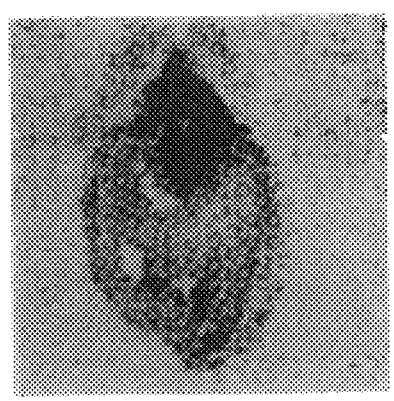
FIG. 1B shows plugs (arrowheads) after excision of the plugs.
Figure 1B:
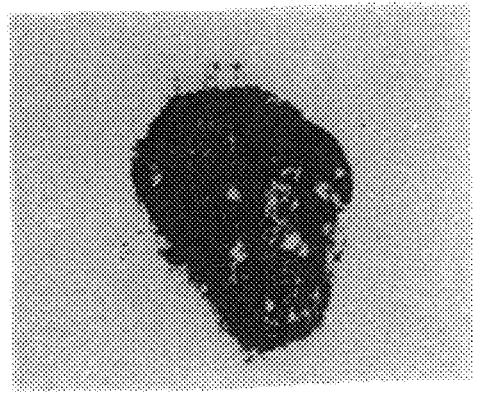

In vivo Assays. Two different in vivo assays were used to evaluate the angiogenic activity of mouse scatter factor. In the first assay, the murine angiogenesis assay, samples mixed with Matrigel, a matrix of reconstituted basement membrane, were injected subcutaneously into mice. After 10 days, the mice were sacrificed for histologic and morphometric analysis of Matrigel plugs. Control plugs were found to be pale pink, while plugs containing scatter factor were found to be bright red and often contained superficial blood vessels (see FIG. 1A and FIG. 1B).

Figure 2A:
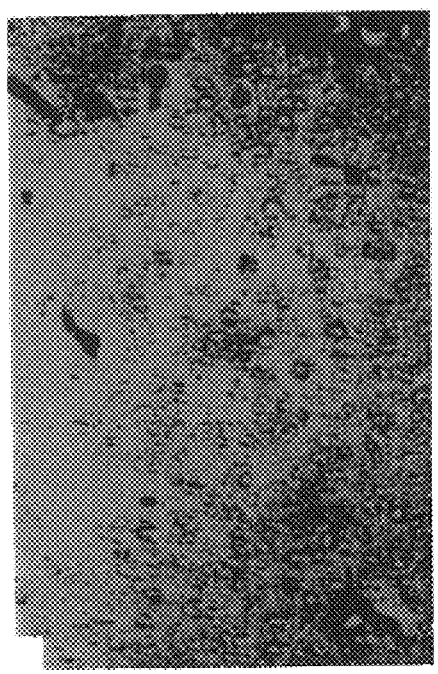
FIG. 2A represents sections of plugs from athymic control (0 ng scatter factor) mice.
Figure 2B:
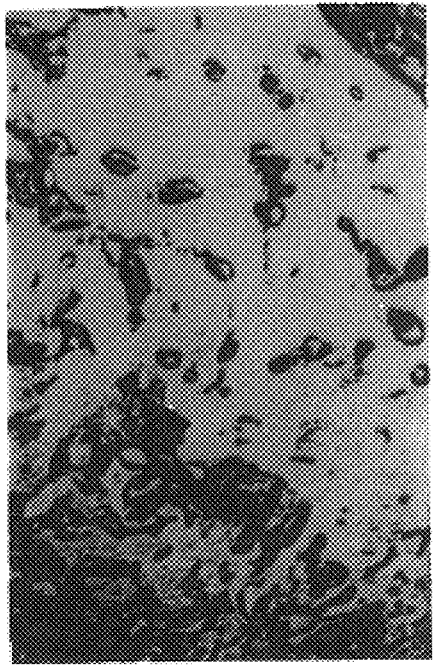
FIG. 2B represents sections of plugs from athymic mice which contain 2 ng scatter factor.
Figure 2C:
FIG. 2C represents sections of plugs from athymic mice which contain 20 ng scatter factor.
Figure 2D:
FIG. 2D represents sections of plugs from athymic mice which contain 200 ng of scatter factor.

Histologic analysis showed little cellularity in control plugs (see FIG. 2A). Plugs containing 2 ng of scatter factor often had increased numbers of cells (see FIG. 2B), 90% of which stained for factor VIII antigen, an endothelial cell marker (not shown) At 20 ng of scatter factor, cell number was increased, and vessels were present (FIG. 2C). At 200 ng of scatter factor, plugs were even more cellular, with endothelial cells making up 50–60% of the cell population. Many large vessels containing smooth muscle cells were seen (see FIG. 2D).

Figure 1C:
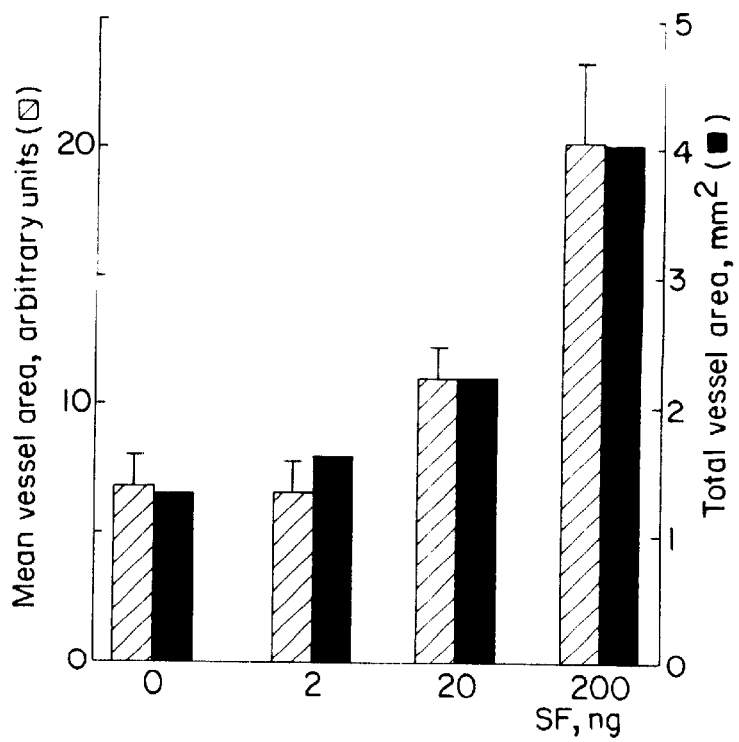
FIG. 1C shows the quantification by digital image analysis for athymic mice.
Figure 1D:
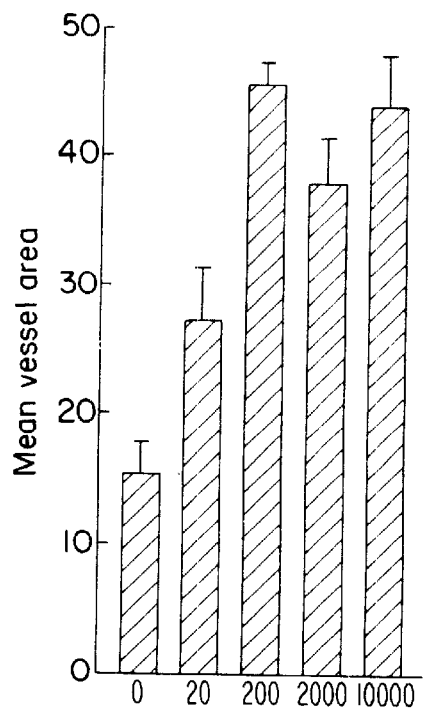
FIG. 1D shows the quantitation by digital image analysis for C57BL mice.

Morphometric analysis of vessel area (see Grant et al., Cell, Vol. 58, pp. 933–943 (1989)) revealed a dose-dependent angiogenic response in athymic (FIG. 1C) and C57BL (FIG. 1D) mice, with half-maximal and maximal responses at about 20 and 200 ng, respectively. Histologic examination at day 10 showed no evidence of inflammation in scatter factor-containing plugs in athymic mice. In C57BL, no inflammation was observed at $\leq 200$ ng of scatter factor, but leukocytic infiltration was present in tissue surrounding the plugs at $\leq 2000$ ng of scatter factor.

Figure 3A:
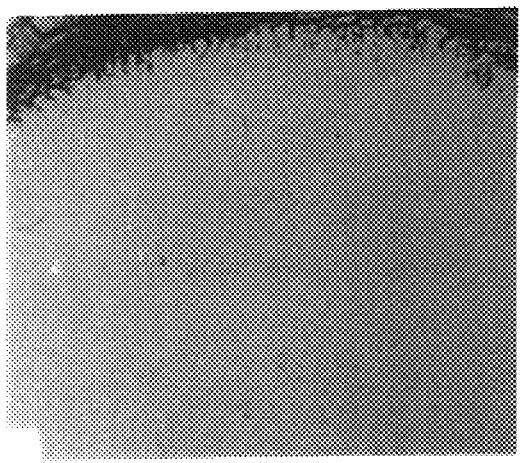
As shown in FIG. 3A, no angiogenic response was observed in control pellets containing PBS.
Figure 3B:
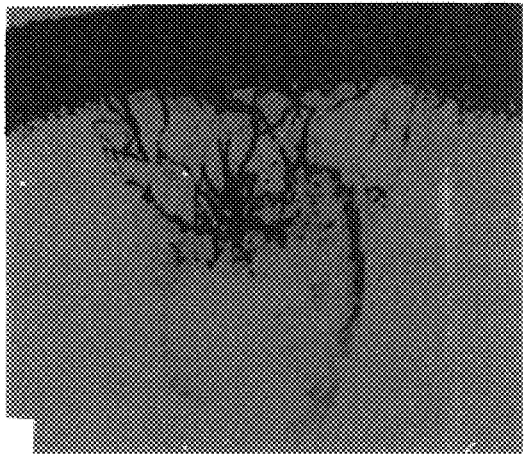
As shown in FIG. 3B, the response for 50 ng scatter factor was positive but weak in comparison with high concentrations of scatter factor.
Figure 3C:
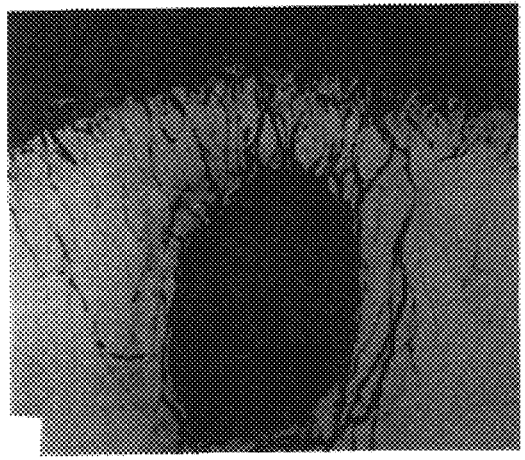
As shown in FIG. 3C, and FIG. 3D, scatter factor concentrations of 100 ng and 500 ng, respectively, gave strong positive responses.
Figure 3D:
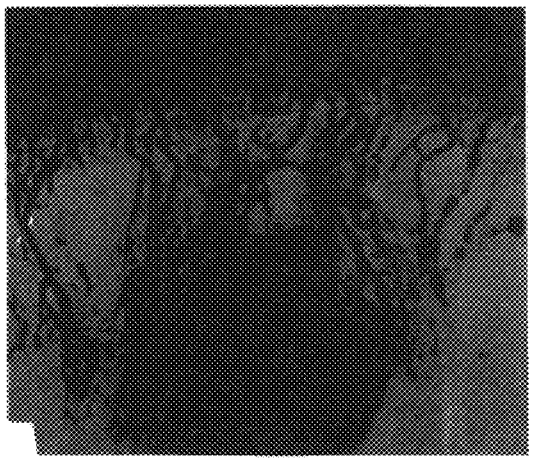
Figure 3E:
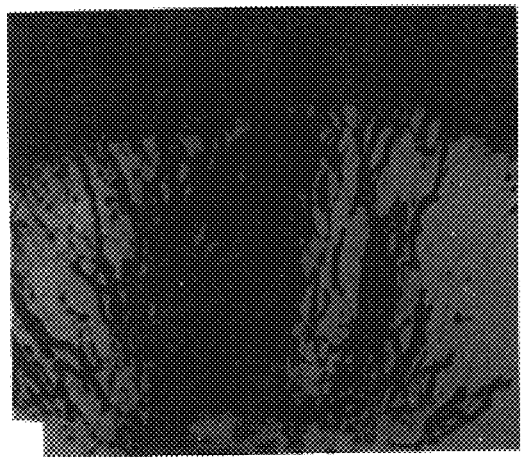
FIG. 3E shows a strong angiogenic response which was induced by 150 ng of basic FGF, a positive control.

In the second assay, samples were implanted in the avascular rat cornea to allow ingrowth of blood vessels from the limbus. Control implants gave no positive responses (see Table 1, below, and FIG. 3A), while implants containing mouse scatter factor induced a dose-dependent corneal neovascularization. Responses at 50 ng (FIG. 3B) were reduced in intensity compared with those at 100 and 500 ng (FIG. 3C and FIG. 3D, respectively). The maximal response to scatter factor was observed at doses of $\leq 100$ ng and was similar to the response to 150 ng of human basic FGF, a positive control (see FIG. 3E).

TABLE 1

Neovascular responses induced in rat corneas by scatter factor (SF)

| Content of pellet | Corneal neovascularization | |
|---|---|---|
| | Positive responses | % |
| Negative controls | | |
| Sham implant | 0/3 | 0 |
| Hydron | 0/2 | 0 |
| PBS | 0/2 | 0 |
| Positive control | | |
| Basic FGF (150 ng) | 4/4 | 100 |
| scatter factor (SF) | | |
| 5 ng | 0.4 | 0 |
| 50 ng | 3/5* | 60 |
| 100 ng | 5/5 | 100 |
| 500 ng | 5/5 | 100 |
| 1000 ng | 5/5+ | 100 |

* Responses were much weaker in intensity compared with implants containing 100 or 500 ng of scatter factor.
+Corneas showed significant inflammation.

rhHGF also induced angiogenesis in the rat cornea (see Table 2, below). At 100 ng, positive responses were observed in four of five implants. At 500 ng of rhHGF, all five implants gave positive responses. Chicken and rabbit antibodies to human placental scatter factor strongly inhibited the angiogenic responses to mouse scatter factor and rhHGF, but not to basic FGF (see Table 2).

TABLE 2

Neovascular responses induced in rat corneas by native mouse scatter factor (SF) and rhHGF with or without antibody (Ab)

| Content of pellet | Corneal neovascularization | |
|---|---|---|
| | Positive responses | % |
| Controls | | |
| Hydron + PBS | 0/8 | 0 |
| Chicken Ab | 0/4 | 0 |
| Rabbit Ab (Ab 978) | 0/3 | 0 |
| Basic FGF (150 ng) | 3/3 | 100 |
| Basic FGF (150 ng) + rabbit Ab | 3/3 | 100 |
| Factor ± Ab | | |
| Mouse SF (100 ng) | 3/3 | 100 |
| Mouse SF (100 ng) + chicken Ab | 1/5* | 20 |
| rhHGF (100 ng) | 4/5 | 80 |
| rhHGF (500 ng) | 5/5+ | 100 |
| rhHGF (100 ng) + chicken Ab | 2/5* | 33 |
| rh HGF (100 ng) + rabbit Ab | 0/5 | 0 |

Antibodies were diluted in PBS. Final dilutions after mixing with Hydron were 1:20 for the chicken antibodies and 1:200 for the rabbit antibodies.
* Responses scored as positive were very weak.
+This concentration of rhHGF was inflammatory.

To assess inflammation, corneas were examined by direct stereomicroscopy daily for the duration of the experiments. Corneas chosen at random were examined histologically at 6, 12 and 24 hours and at 3, 5, and 7 days after implantation of scatter factor and control pellets. Inflammation was not detected at lower angiogenic doses of scatter factor (50–500 ng of mouse scatter factor, 100 ng of rhHGF). At higher doses (50–500 ng of mouse scatter factor, 500 ng of rhHGF), a prominent inflammatory infiltrate was observed. The majority of cells were monocytes and macrophages, as judged by morphology and immunostaining for F4/80, a macrophage/monocyte marker.

Plasminogen activators convert plasminogen into plasmin, a potent serine protease that lyses fibrin clots, degrades components of extracellular matrix, and activates enzymes (e.g., procollagenases) that further degrade matrix (see Saksela et al., Anu. Rev. Cell Biol., Vol. 4, pp. 93–126 (1988)). The inventors have discovered that scatter factor induces large dose-dependent increases in secreted (see FIG. 4A) and cell-associated (see FIG. 4B) plasminogen activator activity in microvascular endothelium (BBEC). Total plasminogen activator activity (secreted plus cell-associated) was increased 4-fold relative to control when scatter factor was present at 20 ng/ml (Z0.2 nM). Similar results were obtained in large vessel endothelium (not shown). Most of the secreted and cell-associated plasminogen activator activity in BBEC was blocked by antibodies to urokinase, but not by antibodies to tissue plasminogen activator (see FIG. 4D and FIG. 4E).

Figure 5A:
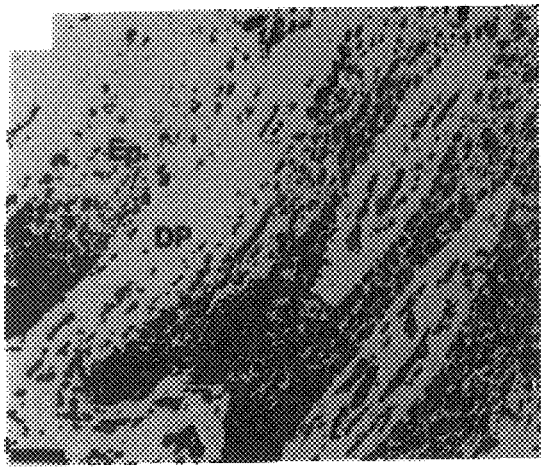
FIG. 5A, FIG. 5B and FIG. 5C show immunohistochemical staining of psoriatic plaques.
Figure 5B:
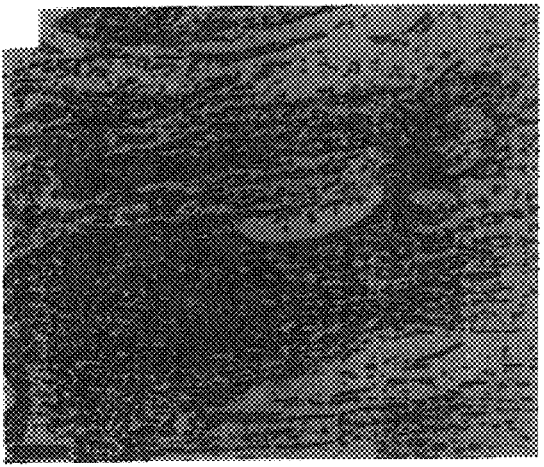
Figure 5C:
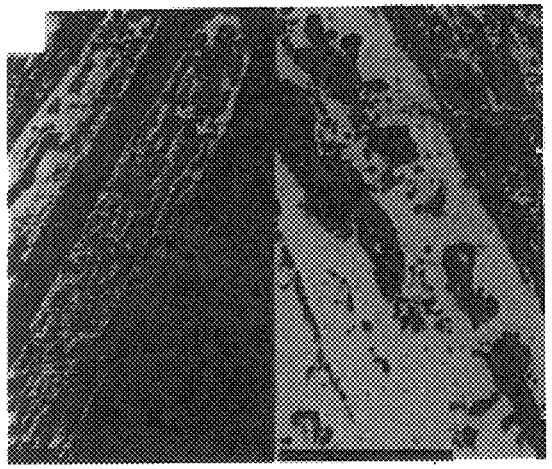
Figure 5D:
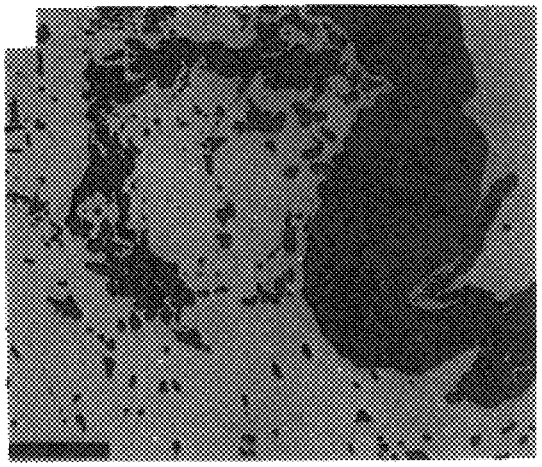
FIG. 5D shows immunohistochemical staining of normal skin from a patient with psoriasis.

Angiogenesis is often associated with chronic inflammation diseases. Psoriasis is a common inflammatory skin disease characterized by prominent epidermal hyperplasia and neovascularization in the dermal papillae. Frozen sections of biopsy samples from psoriatic plaques from 10 patients each showed positive immunohistochemical staining for scatter factor in spindle-shaped and mononuclear cells within the dermal papillae and papillary dermis. Antisera to human placental scatter factor and rhHGF gave an identical staining pattern, as illustrated in FIG. 5A. Scatter factor-positive cells were arranged in a perivascular distribution. Cells of the blood vessel wall did not stain for scatter factor (see FIG. 5C). Normal skin from psoriasis patients or from normal subjects showed little or no staining for scatter factor (FIG. 5D). Sections from psoriatic plaques treated with nonimmune serum as the primary antibody (negative control) showed no staining (FIG. 5B).

Hence, the inventors have determined that physiologic quantities of scatter factor [100–200 ng (Z1-2 pmol)] induced strong angiogenic responses in two in vivo assays. It is likely that this angiogenic activity is due, in part, to direct effects on endothelium since: (i) scatter factor stimulates endothelial migration, proliferation, and tube formation in vitro; (ii) histologic studies showed no evidence of inflammation at scatter factor doses that gave strong angiogenic responses; and (iii) anti-scatter factor antibodies blocked the angiogenic responses. The inventors also found that scatter factor stimulates endothelial cell expression of urokinase. Urokinase, bound to its specific cells surface receptor, is thought to mediate focal, directed, extracellular proteolysis, which is required for endothelial cell invasion and migration during the early stages of angiogenesis.

Growth factors TGFβ, FGF, and platelet-derived growth factor (PDGF) are present in Matrigel and in the matrices of several tissues, including the cornea. The inventors have discovered that combinations of scatter factor and either TGFβ, FGF, or PDGF provide greater stimulation of endothelial tube formation in vitro than did the same agents used individually. The concentrations studied (1 ng/ml) were about 10 times those found in 250 mg of Matrigel, and scatter factor strongly stimulated tube formation on its own, by up to 8 times the amount stimulated by the control.

The major scatter factor producer cells are fibroblasts, smooth muscle cells, and leukocytes. With rare exceptions, responder cells (epithelium, endothelium, melanocytes) are nonproducers. The immunohistochemical studies of psoriatic plaques suggest that scatter factor is produced by cells located outside of the blood vessel wall. Studies by the inventors have indicated that cultured endothelial cells express c-met mRNA and that immunoreactive c-met protein is present in blood vessel wall cells (endothelium and pericytes) in psoriatic plaques. This suggests that scatter factor may play a role in microvessel formation or elongation in psoriasis and that its likely mode of action is paracrine.

Scatter factor (HGF) stimulates motility, invasiveness, proliferation, and morphogenesis of epithelium, and it may be involved in physiologic and pathologic processes such as embryogenesis, wound healing, organ regeneration, inflammation, and tumor invasion. Angiogenesis is a component of each of these processes. Therefore, the in vivo biologic action of scatter factor may be due, in part, to its effects on both epithelial and vascular endothelial cells.

EXAMPLE II

I. Materials and Methods

Cell Lines, Sources, and Culture. MDAMB231 human breast cancer cells and Madin-Darby canine kidney (MDCK) epithelial cells were obtained from the American Type Culture Collection (ATCC), Rockville, Md. Cells were cultured in Dulbecco's Modified Eagle's Medium (DMEM) supplemented with 10% (v/v) fetal calf serum, L-glutamine (5 mM), nonessential amino acids (0.1 mM), penicillin (100 U/ml), streptomycin (100 μg/ml), and fungizone (0.25 μg/ml) (all from Bio Whittaker, Walkersville, Md.). Cells were subcultured weekly as described earlier (Rosen et al., Cancer Res 57: 5315–5321 (1991)). Human dermal microvascular endothelial cells (HDMECs) were purchased from Clonetics, Inc. (San Diego, Calif.) and cultured in EBM Bullet Kit medium (Clonetics), as per the manufacturer's instructions.

Transfection Vectors and DNA Transfection Method. MDAMB231 cells were transfected with human SF cDNA using the vectors and method described earlier (Rong et al., Mol Cell Biol 12: 5152–5158 (1992)). Briefly, the plasmid pRSX24, which was constructed by ligating full-length 2.3 kb SF cDNA into the BamHI-KpnI site of the pMEX vector, was provided by Dr. George Vande Woude (Frederick Cancer Center, Frederick, Md.). Cells were either: (a) co-transfected with pRSX24 plus pSV2neo (Clonetech) (which contains the neomycin-resistance gene); or (b) transfected with pSV2neo alone (control). The calcium phosphate method of DNA transfection was used, exactly as described before (Rong et al., Mol Cell Biol 12: 5152–5158 (1992)). Selection was carried out in culture medium containing 0.4 mg/ml of G418 (Geneticin, GIBCO, Gaithersburg, Md.). Colonies of cells were trypsinized within cloning rings, transferred to 24-well dishes, grown to confluency, and screened for release of SF into serum-free DMEM by ELISA (see below). (SF+neo) clones that produced SF and a number of SF– (neo only) clones were expanded to 12-well and then 100 mm dishes, grown up in the absence of G418, split once, and frozen in liquid nitrogen. (SF+neo) clones that produced the same high levels of SF over multiple (>5) passages were designated SF+ permanent transfectants; and they, along with several SF– (neo only) clones that appeared to proliferate at roughly the same rate were chosen for further study. SF+ and SF– clones were frozen at multiple passages, but only the earliest passage cells were used for injection into animals.

Analysis of Transfected Clones for SF Expression. ELISA Screening of Conditioned Medium (CM). To generate CM, confluent cultures of transfected clones were incubated in serum-free DMEM (0.1 ml/cm$^2$) for 24 hr at 37° C. CM samples were centrifuged (3000 RPM×20 min) to remove debris and stored at –80° C. until the time of assay. Samples were assayed by our standard two-antibody "sandwich" ELISA, as described earlier (Joseph et al., Natl Cancer Inst 87: 372–377 (1995); Rosen et al., J Cell Biol 127: 1783–1787 (1994)). The linear detection range is usually about 0.2 to 4.0 ng/ml of standard [recombinant human SF (rhSF), Genentech, Inc., South San Francisco, Calif.] The assay has been shown to be specific for SF, since plasminogen (closely related to SF) albumin, and a variety of growth factors and cytokines are not detected.

Western Blotting of CM. Twenty-four hour CM samples (see above) from transfected clones were concentrated 10-fold with an Amicon Centricon-lo concentrator (10 kDa cutoff), and 100 μl aliquots were electrophoresed on a 12% non-reduced SDS-polyacrylamide gel. Blots were probed using mouse anti-human SF monoclonal antibody 23C2 (1:2000 dilution of ascites), and bound primary antibody was detected by detected by electrochemiluminescence (ECL) (Amersham), as described before (Rosen et al., J Cell Biol 127: 225–234 (1994)). Recombinant human SF (Genentech) and native human placental SF (Grant et al., PNAS USA 90: 1937–1941 (1993)) were utilized as standards.

Northern Blotting. Probe: A 565 bp portion of human SF cDNA cloned into the BamHI-XhoI fragment of pBluescriptIIKS was provided by Dr. Morag Park (McGill University, Montreal, Canada). The SF cDNA fragment was excised using BamHI and XhoI and labelled with digoxigenin-11-dUTP by the random prime method, using the Genius System DNA Labelling and Detection Kit (Boehringer Mannheim). RNA Isolation, Electrophoresis, Hybridization. Total cell RNA was isolated from near confluent cell cultures by acid guanidinium isothiocyanate-phenol-chloroform extraction. Equal aliquots of RNA (30 μg/lane) were electrophoresed through a 17% formaldehyde-1% agarose gel; transferred to a Nytran membrane overnight in 10×SSC; and UV cross-linked. Prehybridization was carried out for 1 hr at 50° C.; and hybridization was carried out in the same buffer containing 50 ng/ml of probe, overnight, at 50° C. Membranes were washed as follows: 2×SSC, 0.1% SDS, 10 min, 25° C. (twice); and 0.1×SSC, 0.1% SDS, 30 min, 55° C. (twice). Detection: Hybrids were detected using anti-digoxigenin antibody-alkaline phosphatase and an alkaline phosphatase chemiluminescent reaction (Boehringer Mannheim), according to the manufacturer's instructions.

PCR Analysis. Expression of SF and c-met mRNA in SF–transfected and control-transfected cells was assayed by RT-PCR analysis. Total cellular RNA (1 μg) was reverse transcribed using 10,000 U/ml Superscript RNase H-Moloney murine leukemia virus reverse transcriptase (GIBCO BRL), 2.5 mM oligo dT, 5 mM $MgCl_2$, and 1×PCR buffer consisting of 50 mM KCl, 10 mM Tris-HCl, pH 8.3, 1 mM dNTPs, and 1 U/ml RNase inhibitor. The mixture was incubated at 42° C. for 1 hr. heated to 99° C. for 5 min to denature reverse transcriptase, and cooled at 5° C. for 5 min. cDNA from the reverse transcription reaction was subjected to PCR in the presence of 0.15 mM and each of 5' and 3' primers, 1.25 U of Taq polymerase (Perkin-Elmer), 2 mM $MgCl_2$, and 1×PCR buffer. PCR was performed in a DNA thermal cycler (Perkin-Elmer) for 35 cycles, each consisting of 95° C. for 1 min and 60° C. for 1 min. After the 35 cycles, there was a time delay for 7 min at 72° C. The reaction products were visualized by 1.5% agarose gel electrophoresis. The sense and antisense primers, respectively, and the predicted sizes of the RT-PCR reaction products were as follows:

SF: 5'-CAGCGTTGGGATTCTCAGTAT-3' (SEQ ID NO:1), 5'-CCTATGTTTGTTCGTGTTGGA-3' (SEQ ID NO:2), 539 bp.

c-met: 5'-ACAGTGGCATGTCAACATCGCT-3' (SEQ ID NO:3), 5'-GCTCGGTAGTCTACAGATTC-3' (SEQ ID NO:4), 655 bp.

β-actin: 5'-TTGTAACCAACTGGGACGATATGG-3' (SEQ ID NO: 5), 5'-GATCTTGATCTTCATGGTGCTAGG-3' (SEQ ID NO:6), 764 bp.

The SF primers represent the sense sequence in the K3 domain of the α-chain (nucleotide 979–1000) and the antisense sequence in the 5' portion of the β-chain (nucleotide 1497–1518) of the human SF mRNA.

Nude Mouse Assays. Preparation and Injection of Tumor Cells. Clones to be studied were grown to 80–90% of confluence in 150 $cm^2$ dishes and detached with trypsin. The trypsin was neutralized with medium containing serum; and the cells were washed twice by centrifugation, counted, and re-suspended in serum-free DMEM at $0.5\times10^8$ (Experiment 2) or $1\times10^8$/ml (Experiment 3) (see Results). Cells (0.1 ml) were injected into 5–6 wk old female nude mice (Frederick Cancer Research and Development Center, Frederick, Md.). Each animal received two injections, one on each side, in the mammary fat pads between the first and second nipples. For experiment 2, ten injections were made per clone, with $5\times10^6$ cells per injection; and for experiment 3, 20 injections were made per clone, with $1\times10^7$ cells per injection.

Measurement of Tumor Size. The animals were ear tagged; and primary tumor growth was assessed by measuring the volume of each tumor at weekly intervals. Three mutually perpendicular diameters (mm) were measured using a caliper; and the geometric mean diameter was used to calculate the tumor volume in $mm^3$ [ie., $V=(1/6)\Pi(d_1d_2d_3)$]. Only measurable tumors were used to calculate the mean tumor volume for each tumor cell clone at each time point. Animals were sacrificed after 9 (Experiment 2) or 10 wk (Experiment 3), when the largest tumors reached about 20 mm in diameter.

Assessment of Regional Lymph Node and Lung Metastasis. After sacrifice, axillary lymph nodes and both lungs were excised, fixed in formalin, embedded in paraffin, and stained with hematoxylin and eosin (H & E) for microscopic examination for morphologic evidence of tumor metastasis. Sections were reviewed and scored by a board-certified pathologist (AF).

Preparation of Primary Tumors for Additional Studies. Primary tumors were excised and weighed; and half of the tumor was fixed in formalin, while the other half was frozen at −80° C. The formalin-fixed tumor tissue was embedded in paraffin, and 4 μm sections were cut for the immunostaining procedures described below. The frozen tissue was used to prepare protein extracts, as described before (Joseph et al., J Natl Cancer Inst 87: 372–377 (1995)). Tissues were thawed; washed with extraction buffer [20 mM Tris, pH 7.5, 0.5 M NaCl, 0.1 mM PMSF (phenylmethylsulfonyl fluoride)]; cut into pieces; sonicated in ice-cold extraction buffer (4–6 ml/g of tissue); and clarified by microfuging. The precipitate was re-extracted using the same buffer containing 1 M NaCl. [High salt extractions are used to remove growth factors bound to cell surface and matrix.] The two clarified supernatants were pooled and dialyzed against buffer containing 150 mM NaCl. Protein concentrations of extracts were determined using the BioRad Coomassie blue dye-binding microassay (BioRad, Richmond, Va.). Samples were stored at −80° C.

In vitro Assays of Tumor Cell Growth and Motility. Proliferation Curves. See Brief Description of FIG. 8.

Plating (Two-Dimensional Colony-Forming) Efficiency (PE). Exponentially growing cultures of MDAMB231 clones were detached with trypsin, and the trypsin was neutralized with DMEM-10% serum. Cells were counted, serially diluted, and seeded in triplicate at 300 cells per 100 mm dishes in 15 ml of DMEM-10%. Dishes were incubated for 3 wk, after which they were stained with crystal violet, and visible colonies (>50 cells) were counted. The PE (in %) was calculated as [(no. of colonies/300)×100].

Soft Agar Colony Formation. Anchorage independent growth of MDAMB231 clones was assessed using the soft agar assay, as described before (Leone et al., Oncogene 8: 2325–2333 (1993)). Briefly, cells were suspended at $3.75\times10^3$ cells/ml in DMEM-10% serum with 0.36% Bacto-agar (Difco, Detroit, Mich.). Three thousand cells (0.8 ml of suspension) were spread per well over triplicate wells in 6-well dishes containing a hardened plug of DMEM-10% serum with 0.6% agar. Dishes were fed weekly with DMEM-10% serum, and colonies were counted microscopically after 4 wk of incubation. Colony formation was scored as the number of colonies of ≧15 cells per 100 colony forming units.

Urokinase (uPA) and Cell Motility Assays. uPA enzyme activity in conditioned media (CM) from. MDAMB231 clones (see Table 3 legend) was assayed by indirect chromogenic substrate (Spectrozyme) assay, as per the manufacturer's instructions (American Diagnostica, Greenwich, Conn.). High molecular weight human urokinase (80,000 IU/mg) was used as the standard. uPA titers were normalized by CM protein content. Basal motility of MDAMB231 clones was assayed using 96-well Boyden chambers, as described below, in the absence of added chemoattractant. The assay incubation interval was 6 hr, and each clone was assayed in quadruplicate.

In vivo Assays of Tumor Cell Proliferation and Death. Proliferating Cell Nuclear Antigen (PCNA) Index. In vivo tumor cell proliferation was assessed by immunostaining for PCNA, an antigen selectively expressed in cycling cells (Takasaki et al., J Exp Med 154: 1899–1909 (1981)). PCNA was detected by immunoperoxidase staining of paraffin sections of primary tumors with mouse monoclonal anti-human PCNA antibody clone PC-10 (1:200 dilution) (Dako, Carpinteria, Calif.). Each batch of slides stained included human tonsil tissue as a control containing both cycling PCNA positive and resting PCNAnegative cells. The PCNA index (percentage of PCNA positive tumor cells) was determined by counting at least 800 cells per tumor.

Terminal Deoxynucleotidyl Transferase (TdT) Index. In vivo tumor cell apoptosis (programmed cell death) was measured using the recently described method of TdT in situ labelling (Gavrieli et al., *Cell Biol* 119: 493–501 (1992)). TdT labelling was performed on paraffin sections of primary tumors using the In Situ Cell Death Detection Kit from Boehringer Mannheim, Indianapolis, Ind. The TdT index (percentage of apoptotic brown TdT positive nuclei) was determined by counting at least 1000 cells per tumor.

Angiogenesis-Related Studies. Microvessel Counts (MVCs) of Primary Tumors. MVCs in regions of the most active tumor angiogenesis (angiogenic "hot spots") were made by a modification of previously described methods (Weidner et al., *New Engl J Med* 324: 1–8 (1991), JNCI 84: 1875–1887 (1992)). Paraffin sections were stained with anti-laminin antibody (Gibco, Gaithersberg, Md.) (Wolff et al., *Brain Res* 604: 79–85 (1993)); and vessel profiles were counted in 3–4 different areas of tumor containing the highest microvessel density. Two values were determined for each tumor: (a) the peak MVC (single largest number of microvessels per 400×field); and (b) the average peak MVC (mean MVC of the 3–4 400×fields with the largest numbers of microvessels). MVCs were performed in blinded fashion by a board-certified pathologist (AF).

Microvascular Endothelial Cell Chemotaxis Assays. Assays were performed using a modification of the method described earlier (Tolsma et al., *J Cell Biol* 122: 497–511 (1993)). HDMECs between passages 5 to 7 were detached with trypsin; washed three times; counted; resuspended at $1.8 \times 10^6$ cells/ml in DMEM containing 0.1% bovine serum albumin (DMEM-BSA); and inoculated at 28 µl (=$5 \times 10^4$ cells) per well into the lower wells of a 96-well modified Boyden chamber (Neuroprobe, Cabin John, Md.). Wells were covered with an 8 µm pore size Nucleopore filter that was previously coated with 100 µg/ml of Vitrogen in 0.1% acetic acid (Celtrix Laboratories, Palo Alto, Calif.). The chamber was assembled, inverted, and incubated for 2 hr to allow attachment of cells to the underside of the filter. The chamber was then re-inverted, and 50 µl of test materials in DMEM-BSA were added to the upper wells. Chambers were incubated for an additional 5 hr, during which time cells migrated against gravity from the underside of the filter to the upper side of the filter. Non-migrated cells were scraped off the underside of the filter, and filters were stained using Diff-Quick chemicals (Baxter, McGaw Park, Ill.). Migrated cell nuclei were counted using a calibrated ocular grid as cells per 10 high power (400×) grids.

Rat Cornea Angiogenesis Assay. Angiogenesis was assayed in the avascular rat cornea, as before (Polverini and Leibovich, *Lab Invest* 51: 635–642 (1984)). Briefly, test samples were combined 1:1 with a solution of Hydron (Interferon Laboratories, New Brunswick, N.J.) and air-dried overnight. A 5 µl pellet was inserted into a surgically created pocket in the corneal stroma and placed 1–1.5 mm from the limbus. Corneas were examined daily with a dissecting microscope for up to 7 days of capillary growth. Responses were scored as positive if sustained directional ingrowth of capillary sprouts and hairpin loops occurred during the observation period. Responses were scored as negative when no neovascularization was detected or when only an occasional sprout or hairpin loop was observed with no evidence of sustained directional ingrowth. After 7 days, corneas were perfused with colloidal carbon, and whole mount preparations were examined and photographed.

Measurements of Thrombospondin-1 (TSP1) and Vascular Endothelial Cell Growth Factor (VEGF). The TSP1 content of tumor extracts was measured using a specific and sensitive two antibody ELISA similar to that utilized to measure SF (Joseph et al., *J Natl Cancer Inst* 87: 372–377 (1995)). The first (coating) antibody was anti-human TSP1 mouse monoclonal B7 (1:2000 dilution) (Sigma Chemical Corp., St. Louis, Mo.); and the second (recognizing) antibody was rabbit anti-human TSP1 antiserum (1:2000). The assay detected as little as (2.5–5) ng/ml of TSP1 standard (GIBCO), and did not detect any of a variety of cytokines, growth factors, and extracellular matrix molecules at 500 or 1000 ng/ml. VEGF content of tumor extracts was determined using a specific and sensitive two-antibody VEGF ELISA (Koch et al., *J Immunol* 152: 4149–4156 (1994)).

Statistical Analysis. Values were expressed as means±standard errors of the mean (SEMs); and comparisons were made using the two-tailed Student's t-test. Where appropriate, the chi-squared test was used to compare proportions.

Expression of Scatter Factor in normal ischemic tissue. In order to ascertain potential expression of HGF using the plasmid PRSX24 on normal ischemic tissue, Srague-Dawley rats weighing 210–300 were anesthetized, intubated and placed on a positive-pressure respirator. The left coronary artery was ligated 3–4 millimeters from its origin to produce mycardial infarction, and at the same time, the apices of the heart were injected with 40 micrograms of the PRSX24 (HSF) plasmid.

Expression analysis was performed using antihuman HGF monoclonal antibodies by analyzing cross-sectional sections of the apex of rat hearts using immunochemistry techniques. Five days following injection of the plasmid, positive staining was seen in the myocardium which supports expression of HSF in the tissue.

II. Results

Transfection and Characterization of Transfected Cell Clones. MDAMB231 parent cells were transfected using either: (a) separate vectors containing full-length SF cDNA (pRSx24) and the neomycin resistance gene (pSV2neo) (SF+neo); or (b) the neomycin vector pSV2 alone (neo only).

Single-cell SF− transfectant (SF+neo) clones and control (neo only) clones were generated by selection in G418. Clones were screened by ELISA for SF released into serum-free medium during a 24 hr incubation. Six (SF+neo) clones were found to produce SF titers (9–100 ng/ml) more than twice as high as high producer MRC5 human lung fibroblasts (4 ng/ml) In contrast, none of 20 (neo only) clones produced any detectable SF. Two high SF− producing (SF+) clones (21 and 29) and two SF− (neo only) clones (32 and 34) (SF−) that appeared to proliferate at roughly the same rate as the SF+ clones were chosen for further study.

Figures 6A, 6B:
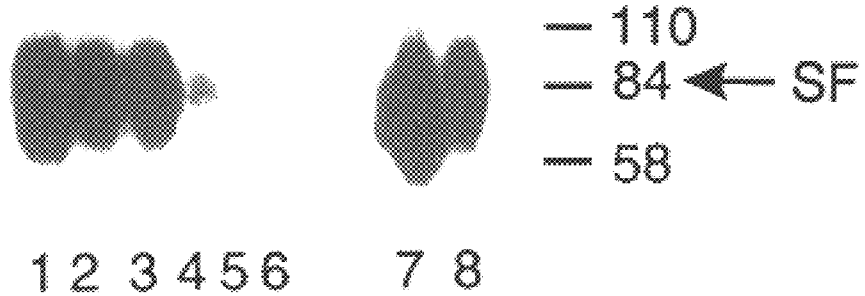
FIGS. 6A and 6B. Production of SF by SF-transfected and control MDAMB231 cells.
Figure 7:
FIG. 7. Expression of SF and c-met mRNA in MDAMB231 cell clones by RT-PCR analysis. The 539 bp SF reaction product was detected in SF transfected clone 21 (lane 1) and 29 (lane 2), but not in control transfected clone 32 (lane 3) and 34 (lane 4). However, the 655 bp c-met reaction product and the 764 bp β-actin product were detected in all four clones.
Figure 7:
Figure 7:

These clones were characterized for expression of SF protein, biologic activity, and mRNA. SF+ clones 21 and 29 produced high levels of immunoreactive SF protein [by ELISA (Table 3) and Western blotting (FIG. 6A)] and high levels of SF bioactivity [by MDCK serial dilution scatter assay (Table 3)]. In contrast, SF− clones 32 and 34 produced no detectable SF by any of these assays. On Northern blotting (FIG. 6B), SF+ clones 21 and 29 exhibited a single mRNA band consistent with the size of the 2.3 kb SF cDNA; while control clone 34 gave no hybridizing mRNA bands (clone 32 was not tested by Northern analysis). RT-PCR analysis confirmed that clones 21 and 29 expressed SF mRNA, while clones 32 and 34 did not express any detectable SF mRNA (FIG. 7). All four clones expressed mRNA for the c-met receptor, although mRNA expression was slightly lower for clone 32. SF+ clones 21 and 29 also showed a strong in situ hybridization signal using an antisense SF riboprobe, with little or no signal using the corresponding sense riboprobe (data not shown). These assays indicate high level expression of the SF cDNA in SF+ clones 21 and 29 and no detectable expression in control (neo only) clones 32 and 34.

Figure 8:
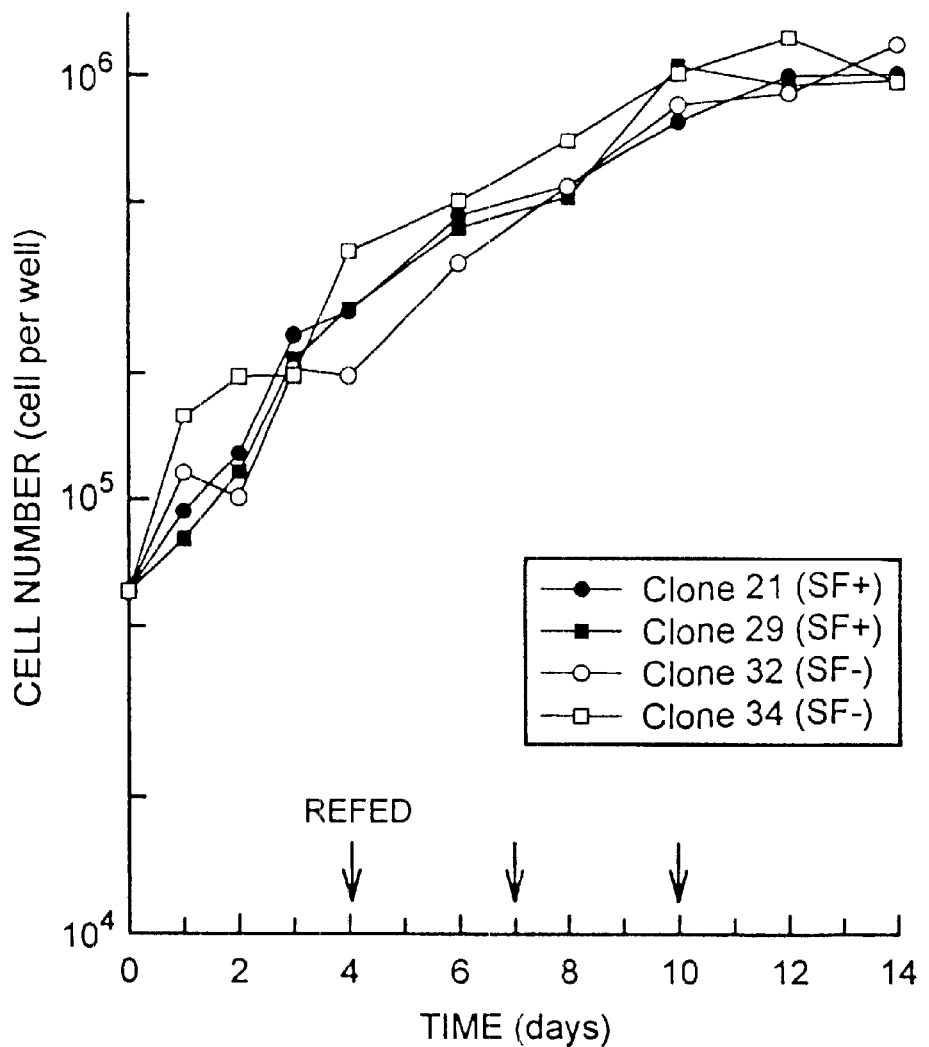
FIG. 8. In vitro proliferation kinetics of scatter factor (SF) transfected and control MDAMB231 human mammary carcinoma cell clones. Sixty thousand cells/well were seeded into 12-well dishes on day −1 and allowed to overnight in 1.0 ml of DMEM plus 5% serum. Medium was replaced on day 0 and on the days indicated, and wells were counted in duplicate by hemacytometer, as indicated. Each point is a mean of duplicate assays, with a range of ±10% of the mean value.

In vitro Growth and Motility Characteristics of SF+ Vs SF− Cell Clones. In standard two-dimensional proliferation assays, SF+ clones (21 and 29) showed similar growth kinetics to SF− clones (32 and 34) and reached similar saturation densities (FIG. 8). The plating efficiency (PE) (two-dimensional colony formation),is a measure of the proportion of cells capable of "unlimited proliferation" (defined as formation of a visible, stainable colony) at clonal density. The PE of SF+ clone 21 was lowest (17%); that of SF+ clone 29 and SF− clone 34 were similar (45% and 44%); while SF− clone 32 had an intermediate PE value (30%) (Table 3). The average PE values were 31% for SF+ clones vs 37% for SF− clones. Clones 21, 29, and 32 did not form colonies in soft agar during a standard four week assay; while clone 34 formed only a handful of colonies. Thus, none of the clones were capable of a significant degree of anchorage independent growth.

SF is known to induce motility and invasiveness of many human carcinoma cell lines (Stoker et al., *Nature* 327: 238–242 (1987); Rosen et al., *Inv Metastasis* 10: 49–64 (1990), *Cancer Res* 57: 5315–5321 (1991), *Int J Cancer* 57: 706–714 (1994); Weidner et al., *J Cell Biol* 111: 2097–2108 (1990)). Morphologically, cultures of SF+ cells appeared "scattered" (ie. showed cell dissociation and fibroblastic morphologic changes), as compared with cultures of SF− cells (data not shown). SF+ clones produced higher titers of urokinase, an enzyme associated with cell invasion, than did SF− clones (Table 3). SF+ clones also showed higher rates of random motility, assayed in chemotaxis chambers in the absence of exogenous chemoattractant (Table 3). These studies indicate that SF+ clones do not exhibit any in vitro growth advantage relative to SF− clones but do exhibit a more motile and invasive phenotype.

In vivo Tumor Growth of SF+ vs SF− Clones in Nude Mice. Tumorigenicity reflects the ability of tumor cells to generate tumors upon injection into appropriate animal hosts, and is not the same as primary tumor growth. In these studies, the parent cell line (MDAMB231), obtained from the ATCC, had not been pre-adapted or selected for in vivo tumor growth. In a pilot study (Experiment 1), injection of $4 \times 10^5$ cells yielded a tumor take rate (judged after 3 wk) of 8/20 (40%) for SF+ clones (21+29) and 3/20 (15%) for SF− clones (32+34). In Experiment 2, $5 \times 10^6$ cells were injected, and tumor take rates were 16/18 (89%) for clones (21+29) and 9/18 (50%) for clones (32+34). In Experiment 3, $10 \times 10^6$ cells were injected, and the tumor take rates were 39/40 (98%) for clones (21+29) and 36/38 (95%) for clones (32+34). These findings suggest that the SF− clones are "not quite tumorigenic" in terms of their in vivo growth, and both SF+ and SF− cells require large initial innocula [$(5–10) \times 10^6$ cells per injection] to generate tumors.

Figure 9A:
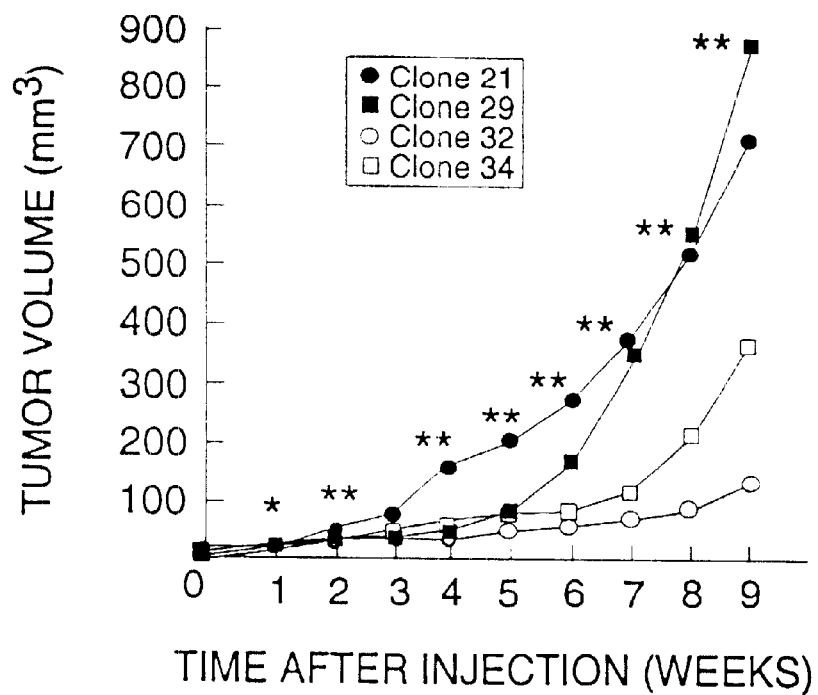
FIGS. 9A and 9B. In vivo tumor growth of SF− transfected and control clones of MDAMB231 human mammary carcinoma cells in the mammary fat pads of nude mice. Cells were injected at time 0 into the mammary fat pads, and tumor volumes were determined each week from measurements of three perpendicular diameters. [See Materials and Methods for details, including numbers of cells and animals injected.]
Figure 9B:
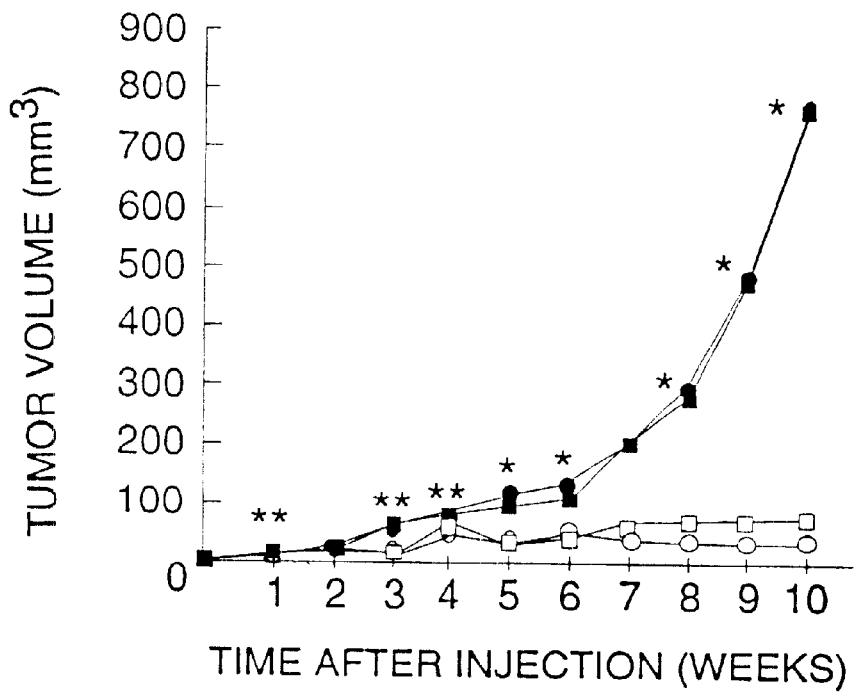

Primary Tumor Growth. Tumors generated from SF+ clones (21 and 29) showed significantly increased growth rates in all three experiments, as compared with tumors from SF− control clones (32 and 34). Tumor growth curves from two experiments are shown in FIG. 9A (Experiment 3) and FIG. 9B (Experiment 2). Experiments were carried out for 9–10 weeks, by which time the largest tumors had reached about 2 cm in diameter. In one experiment (FIG. 9A), SF+ clone 29 tumors showed similar growth to the SF− tumors until week 5, after which it overtook both SF− clones. In the other experiment (FIG. 9B), both SF+ clone tumors were consistently larger than both SF− clone tumors. At sacrifice, the weights of SF+ tumors were significantly greater than those of SF− tumors (P<0.001), by a ratio similar to that of the primary tumor volumes (Table 4). Thus, while caliper measurements of tumor size may include skin tissue, these measurements are still likely to reflect tumor size.

Regional and Metastatic Tumor Dissemination. To study tumor dissemination, H & E stained paraffin sections of axillary lymph nodes and lungs were examined for morphologic evidence of tumor cells by light microscopy. SF+ clones showed a higher proportion of lymph node positivity (37%) than did SF− clones (13%) (P =0.011, chi-squared test) (Table 4). On the other hand, neither SF+ nor SF− clones gave rise to lung metastases the presence of occasional isolated tumor cells in some of the lung samples cannot be ruled out, it was generally easy to observe a small cluster of tumor cells in the murine nodes. In representative nodes scored as positive by tumor cell morphology, immunochemical staining with human pre-keratin antibody (which stains adenocarcinoma) revealed an intense positive ring of cytoplasmic staining within the tumor cells (data not shown).

Additional Studies. Thus, SF+ clones grew more rapidly as tumors and showed a higher rate of lymph node metastasis than did SF− clones, despite the lack of an in vitro proliferative advantage for the SF+ cells. Additional studies were performed to investigate the discrepancy between these in vivo and in vitro results.

Expression of SF in vivo in Tumors. To confirm that SF+ and SF− clones maintained their respective SF producing phenotypes in vivo, tumors were excised after the animals were sacrificed, and protein extracts were prepared and assayed for SF by ELISA. These studies revealed that extracts of SF+ clone (21+29) tumors had about 50-fold higher SF content than did extracts of SF− clone (32+34) tumors (43 vs 0.9 ng SF/mg protein), confirming high level SF production in vivo in SF+ tumors (Table 5). Secondly, five different SF+ clone 21 tumors and five SF+ clone 29 tumors, were explanted into cell culture, selected in G418 to kill host stroma, passaged several times to obtain what appeared to be pure tumor cell cultures, and tested for release of SF into serum-free culture medium. The SF+ clones all produced very high SF titers, similar to those of primary clones that had not been through in vivo passage. One of these secondary clones (SF+ clone 29-1L) was re-injected into nude mice and exhibited in vivo growth as fast as or faster than primary SF+ clone 21 or clone 29 (data not shown).

PCNA Index. PCNA is an antigen expressed selectively in cycling cells, during the late G1 to M phase (Takasaki et al., *J Exp Med* 154: 1899–1909 (1981)). The PCNA index (percentage of PCNA positive cells detected by immunohistochemical staining) is a measure of the percentage of cycling cells within a tissue. To determine if SF+ tumors have a higher proportion of cycling cells than SF− tumors, paraffin-embedded primary tumor sections were immunostained with anti-PCNA antibody. A modest but significant increase in the PCNA index of SF+ vs SF− tumors was found (70% vs 60%, P<0.01) (Table 6).

TdT Labeling Index. TdT in situ labeling is a recently described method by which apoptosis can be assessed in tissue sections (Gavrieli et al., *J Cell Biol* 119: 493–501 (1992)). Apoptosis in normal tissues and tumors may have a major impact on steady-state maintenance and on growth rates (Wyllie, *Cancer Metastas Rev* 11: 95–103 (1992); Holmgren et al., Nature Medicine 1: 149–153 (1995)). Thus, increased rates of apoptosis in SF− relative to SF+ tumors could contribute to more rapid overall growth of the latter. TdT labeling of primary tumor sections was performed and the percentage of apoptotic single cells within the mass of surrounding viable cells (TdT labeling index) was determined. This analysis revealed that the TdT indices were similar in SF+ vs SF− tumors, and these indices were very low for all four clones (ca. 1%) (Table 6). Thus, it is unlikely that differential rates of apoptosis can explain observed differences in tumor growth.

Angiogenesis-Related Studies. Microvessel Counts (MVCs) of Primary Tumors. Recent studies suggest that MVCs of paraffin sections of human breast cancers and other tumor types can be utilized as a measure of tumor angiogenesis, and that these MVC measurements are independent markers of prognosis (Weidner et al., *New Engl J Med* 324: 1–8 (1991), *JNCI* 84: 1875–1887 (1992)). The MVC method involves counting the number of immunostained microvessel profiles per unit area in the region of tumor containing the most active tumor angiogenesis and thus reflects vessel formation in "angiogenic hot spots". MVCs in SF+ vs SF– primary tumors were measured as both the highest individual MVC ("peak MVC") and the average MVC of 3–4 fields with the highest vessel densities ("average peak MVC"). It was found that SF+ tumors (21 and 29) had 60–70% higher peak and average peak MVCs as compared with SF– tumors (32 and 34) (Table 7). Statistical comparison of pooled MVC results for clones (21+29) vs clones (32+34) revealed P<0.001 for both peak MVC and average peak MVC (two-tailed t-test). Thus, using MVC as the criterion, SF+ tumors exhibited more tumor angiogenesis than did SF– tumors.

Figure 10A:
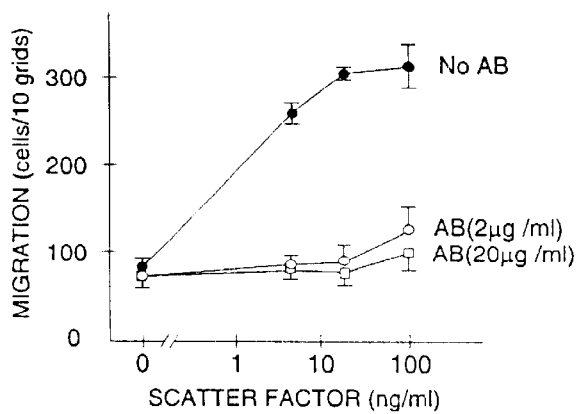
FIGS. 10A–10E. Human dermal microvascular endothelial cell (HDMEC) chemotaxis assays.
Figure 10B:
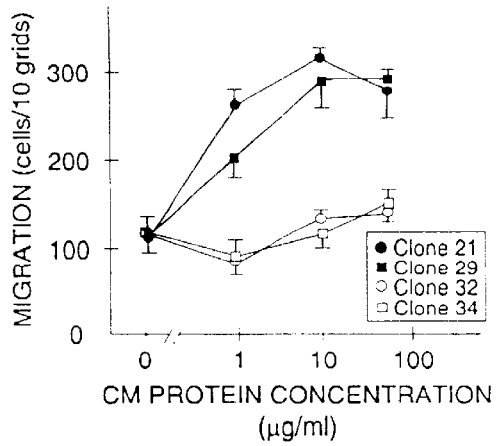
Figure 10C:
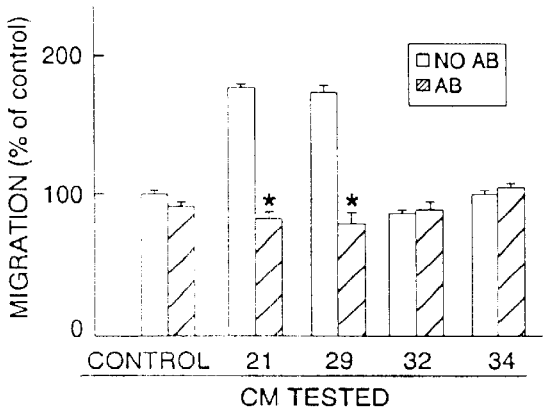

Microvascular Endothelial Cell Chemotaxis Assays. Chemotactic activity for microvascular endothelial cells is an in vitro correlate of in vivo angiogenic activity (Tolsma et al., *J Cell Biol* 122: 497–511 (1993)). In different batches of HDMEC cells, rhSF gave (2.5–10)-fold stimulation of chemotaxis, with maximal responses at 5–10 ng/ml and half-maximal responses at about 0.5 ng/ml of SF. In the presence of 20 $\mu$g/ml of anti-SF neutralizing monoclonal MO294 (R & D Systems), more than 90% of the SF–stimulated chemotactic migration was reproducibly inhibited at 20 ng/ml of SF and 80–85% of the stimulated migration was inhibited at 100 ng/ml of SF (FIG. 10A). Conditioned medium (CM) from SF+ cultured mammary carcinoma clones 21 and 29 (normalized by secreted protein content) gave dose-dependent stimulation of chemotaxis of HDMECs, whereas CM from control SF– clones 32 and 34 gave little or no stimulation of HDMEC chemotaxis (FIG. 10B). All of the stimulated chemotactic migration induced by clone 21 and 29 CM was blocked by MO294, which had no effect on migration in the presence of clone 32 and 34 CM (FIG. 10C). These findings indicate that SF– transfection enhances the net angiogenic balance of the cultured mammary carcinoma cells.

Figure 10D:
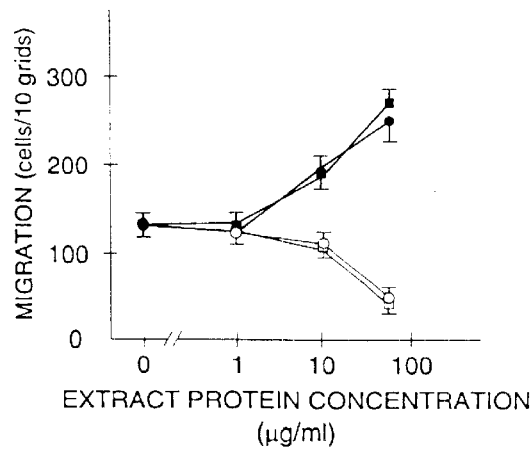
Figure 10E:
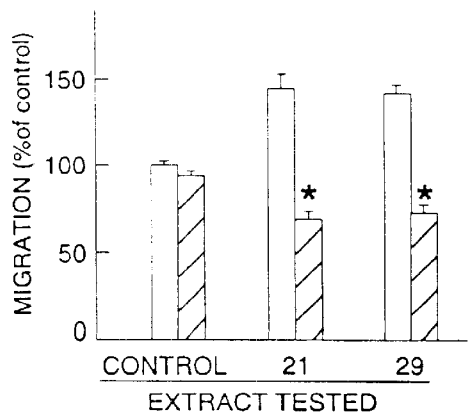

To assess the angiogenic phenotype of the actual tumors, protein extracts form tumors excised at the end of the experiment were assayed for HDMEC chemotactic activity. Extracts from clones 21 and 29 showed definite chemotactic activity, while extracts from clones 32 and 34 showed no activity (FIG. 10D). In tests of other extracts at 50 $\mu$g/ml, SF+ tumors reproducibly gave greater than control chemotactic migration, while SF– tumors always gave less than control migration. The latter finding might be due to the presence of an inhibitor or to toxicity of the extract. The enhanced chemotactic activity in 50 $\mu$g/ml of clone 21 and 29 tumor extracts was neutralized to below control levels (about 75% of control) by anti-SF monoclonal (FIG. 5E). Again, this observation may reflect the presence of an inhibitor or toxin in the extract preparation.

Figure 11A:
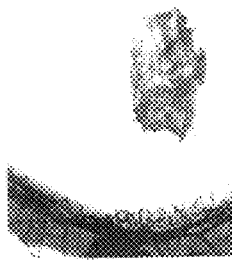
FIGS. 11A–11E. Angiogenic activity of primary tumor extracts from SF+ and SF− tumors in the rat cornea. A 5 µl pellet of Hydron containing test samples was inserted into the avascular rat cornea about 1–1.5 mm from the limbus. After 7 days, corneas were perfused with colloidal carbon, and whole mount preparations were photographed.
Figure 11B:
Figure 11C:
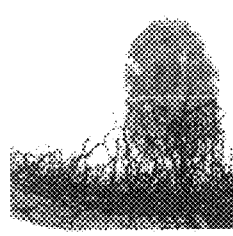
Figure 11D:
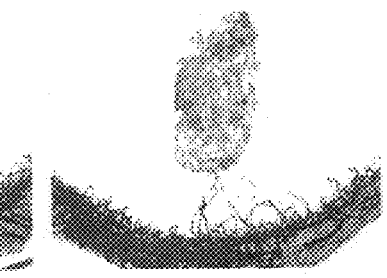
Figure 11E:
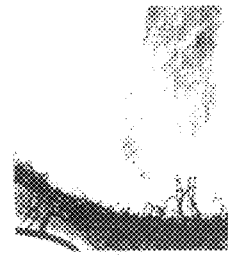

Rat Corneal Neovascularization Assay. The rat cornea assay (27) was used to assess in vivo angiogenic activity in tumor extracts (Table 8 and FIGS. 11A–11E). As observed before (15), recombinant human SF, a positive control, gave a positive neovascular response (FIG. 11B) that was blocked by neutralizing anti-SF antibody (Table 8). Extracts from an SF+ clone 21 tumor also gave strong positive responses (FIG. 11C) that were inhibited by anti-SF antibody (FIG. 11E). On the other hand, extracts from an SF– clone 32 tumor yielded weakly positive responses (FIG. 11D) that were not inhibited by anti-SF antibody. Thus, under the conditions of this assay, extracts from both SF– transfected and control tumors exhibited detectable angiogenic activity, but the SF+ transfected tumors had higher levels of angiogenic activity than did the control transfected tumors.

VEGF and TSP1 Assays of Extracts of Primary Tumors. To determine if expression of angiogenic regulatory molecules other than SF differed in SF+ vs SF– tumors, levels of the angiogenic growth factor VEGF and the anti-angiogenic macromolecule TSP1 were measured in tumor extracts. Each SF– tumor clone (32 and 34) had higher VEGF content than each SF+ clone (21 and 29) (P<0.001) (Table 5). However, the observed titers of VEGF (0.1–0.5 ng/mg protein) were two orders of magnitude lower than SF– titers in SF+ tumors (40 ng/mg protein). CM was also tested from the cultured cell clones and found similar results: clones 32 and 34 CM contained more immunoreactive VEGF by Western blotting than did clone 21 and 29 CM (data not shown). Assays of TSP1 revealed that the most rapidly growing tumor (SF+ clone 29) had the lowest TSP1 content, while the slowest growing tumor (SF– clone 32) had the highest TSP1 content (P<0.001, clone 29 vs 32) (Table 5). However, clone 21 (SF+) and 34 (SF–) tumors had similar, intermediate levels of TSP1.

TABLE 3

In Vitro Characteristics of Scatter Factor (SF)-Transfected and Control Clones

| Clone | SF Production | | | Soft agar | uPA Productions | Migration |
| --- | --- | --- | --- | --- | --- | --- |
| | (ng/ml) | (units/ml) | PE(%) | colonies | (IU/mg protein) | (cells/10 grids) |
| 21(SF + neo) | 56 | 128–256 | 17 ± 0 | 0 | 283 | 362 ± 8 |
| 29(SF + neo) | 43 | 128–256 | 45 ± 2 | 0 | 501 | 377 ± 9 |
| 32(neo) | 0 | 0 | 30 ± 1 | 0 | 123 | 174 ± 5 |
| 34(neo) | 0 | 0 | 44 ± 3 | 2 | 89 | 190 ± 5 |

PE = Plating efficiency; uPA = Urokinase.
To measure SF production, confluent cultures were incubated in serum-free DMEM (0.1 ml/cm$^2$) for 24 hours, and the conditioned media (CM) were assayed for immunoreactive SF by ELISA (ng/ml) and for SF bioactivity using the MOCK serial dilution scatter assay (units/ml). PE is the percentage of cells that form visible, stainable two-dimensional colonies after 3 weeks of incubation; values listed are means ± SEM of triplicate determinations. Soft agar colony formation is the number of three-dimensional colonies of ≧15 cells per 100 colony forming units after 4 weeks. uPA enzyme activity was measured in CM and normalized per mg of CM protein. Migration values were measured in 96-well modified Boyden chambers in the absence of chemoattractant and represent means ± SEM of quadruplicate assay.

TABLE 4

Primary Tumor Size, Lymph Node Status, and Lung Metastases at Time of Killing

| Clone | Primary tumor weight(g) | Primary tumor volume(mm³) | Lymph nodes pos/total(%) | Lung metastases pos/total(%) |
|---|---|---|---|---|
| 21 | 0.76 ± 0.11(25) | 723 ± 93(25) | 6/24(25%) | 0 |
| 29 | 1.01 ± 0.24(17) | 866 ± 193(17) | 9/17(63) | 0 |
| 32 | 0.19 ± 0.05(16) | 121 ± 22(16) | 2/15(13) | 0 |
| 34 | 0.36 ± 0.08(16) | 321 ± 67(16) | 2/15(13) | 0 |

Weights and volumes are expressed as means ± SEM (number of tumors assayed). Statistical comparisons of pooled data for SF+ tumors (clone 21 + 29) versus SF− tumors (32 + 34); tumor weight, $p > 0.001$ (two-tailed t-test); tumor volume, $p > 0.001$ (two-tailed t-test); lymph node positivity, $p = 0.011$ (chi-squared test).
Pos = Positive.

TABLE 5

Content of Angiogenesis Regulatory Factors in Primary Tumor Extracts[1].

| Clone | SF Content (ng SF/mg protein) | VEGF Content (ng/mg protein) | TSP1 Content (ng TSP1/mg protein) |
|---|---|---|---|
| 21 | 39.3 ± 3.2(25) | 0.13 ± 0.02(4) | 485 ± 68(17) |
| 29 | 47.4 ± 3.8(17) | 0.17 ± 0.03(4) | 283 ± 67(13) |
| 32 | 1.1 ± 0.3(16) | 0.51 ± 0.14(4) | 1396 ± 330(14) |
| 34 | 0.8 ± 0.3(16) | 0.48 ± 0.10(4) | 481 ± 81(11) |

[1]Abbreviations: SF = scatter factor; VEGF = vascular endothelial growth factor; TSP1 = thrombospondin-1. Primary tumors tested were from Experiments 2 + 3 for SF and Experiment 3 for VEGF and TSP1. Values listed are means ± SEMs (number of tumors assayed). For SF, statistical comparison of pooled clones (21 + 29) vs (32 + 34) gave $P < 0.001$. For VEGF, comparisons of pooled clones (21 + 29) vs (32 + 34) gave $P < 0.001$. For TSP1, values for clone 32 were significantly greater than those for clones 21($P < 0.01$), 29($P < 0.001$), and 34($P = 0.027$). TSP1 values for clone 29 were lower than those for clones 21($P = 0.046$), 32($P < 0.001$), and 34($P = 0.07$).

TABLE 6

Cell Proliferation (PCNA Index), and Cell Death (TdT Index) In Vivo in Primary Tumors[1].

| Clone | PCNA Index (% Positive Cells) | TdT Labeling Index (% Positive Cells) |
|---|---|---|
| 21 | 69 ± 2(15) | 0.8 ± 0.1(22) |
| 29 | 71 ± 2(13) | 1.0 ± 0.1(16) |
| 32 | 57 ± 6(14) | 1.0 ± 0.2(16) |
| 34 | 63 ± 4(12) | 0.9 ± 0.1(12) |

Abbreviations. PCNA = proliferating cell nuclear antigen; TdT = terminal deoxytransferase. Values listed are means ± SEMs (number of tumors assayed). PCNA and TdT indices were determined from staining of paraffin sections of tumors. Staining and counting procedures are described in Materials and Methods. For TdT, values were derived from Experiments 2 + 3; for PCNA, values were derived from Experiment 3. Statistical comparison of pooled clones (21 + 29) vs (32 + 34) gave: $P < 0.001$ (SF content); $P = 0.006$ (PCNA index); and $P > 0.1$ (TdT index).

TABLE 7

Microvessel Counts (MVCs) of Primary Tumors[1].

| Clone | Peak XVC | Average Peak XVC |
|---|---|---|
| 21 | 6.4 ± 0.4(23) | 4.7 ± 0.3(23) |
| 29 | 6.4 ± 0.8(17) | 4.6 ± 0.5(17) |
| 32 | 4.1 ± 0.5(15) | 3.2 ± 0.4(15) |
| 34 | 3.5 ± 0.5(15) | 2.5 ± 0.3(15) |

[1]Tumor sections were stained and examined for microvessels as described in Materials and Methods. Peak MVC is the number of microvessels per field (40X objective, 10X ocular) in the region of most active tumor angiogenesis. Average peak MVC is the mean MVC of the 3–4 fields with the highest microvessel counts. Values listed are means ± SEMs (number of tumors assayed). Comparisons of pooled clones (21 + 29) vs (32 + 34) gave $P < 0.001$ (peak MVC) and $P < 0.001$ (average peak MVC).

TABLE 8

Angiogenic Responses Induced by SF-Transfected and Control Human Breast Cancer Extracts

| Test sample | Corneal neovascularization proportion of positive responses (%) |
|---|---|
| Controls | |
| Hydron + PBS | 0/4 (0) |
| SF (50 ng) | 4/4 (100) |
| M0294 (500 ng) | 0/3 (0) |
| SF (50 ng) + M0294 (2.5 µg) | 0/3 (0) |
| Tumor extracts ± M0294 | |
| SF+ Clone 21 (5 µg) | 4/4 (100) |
| SF+ Clone 21 + M0294 | 1/4 (25) |
| SF− Clone 32 (5 µg) | 1/3* (33) |
| SF− Clone 32 + M0294 | 1/4* (25) |

SF = Recombinant human scatter factor; M0294 = Anti-SF-neutralizing monoclonal.
*Assay methods and response criteria are described in "Materials and Methods." Neovascular responses induced by SF− tumor extracts with or without M0294 were substantially weaker in intensity than responses induced by SF+ extracts.

III. Discussion

The inventors have shown that transfection of SF cDNA into the human breast cancer cell line MDAMB231 results in an increased rate of orthotopic tumor growth in nude mice of tumors derived from SF+ cell clones as compared with SF− (control) cell clones. Tumors derived from SF+ clones also had significantly higher rates of spread to regional lymph nodes; but neither SF+ nor SF− clones gave any detectable pulmonary metastases. The SF+ clones overexpressed SF mRNA and overproduced SF protein in vitro in cell culture and in vivo in tumors. In contrast, SF− clones produced little or no SF in vitro or in vivo. Thus, it is unlikely that the lack of SF production by SF− control clones and by parental MDAMB231 cells was due to absence of a required factor(s) in the cell culture environment that is present in the in vivo environment. Moreover, SF+ clones did not show any in vitro growth advantage over SF− clones, as indicated by assays of proliferation kinetics, plating efficiency, and soft agar colony formation.

SF+ clones showed scattering, increased in vitro cell motility, and increased urokinase production as compared with SF− clones. These findings are consistent with the observation that MDAMB231 cells express the c-met receptor and with many previous observations that SF up-regulates the motile and invasive phenotype of epithelial and carcinoma cells (Stoker et al., *Nature* 327: 238–242 (1987); Rosen et al., *Inv Metastasis* 10: 49–64 (1990), *Cancer Res* 57: 5315–5321 (1991), *Int J Cancer* 57: 706–714 (1994); Weidner et al., *J Cell Biol* 111: 2097–2108

(1990)). In a prior study of mouse 3T3 cells, it was shown that transfection of human SF plus human c-met cDNAs induced a highly tumorigenic phenotype via an autocrine loop (Rong et al., *Mol Cell Biol* 12: 5152–5158 (1992)). A similar autocrine loop may have contributed to the increased tumorigenicity and to the increased rate of dissemination to axillary lymph nodes of SF+ human breast cancer clones relative to SF− clones. However, it is unlikely that autocrine stimulation per se contributed to the increased growth rate of SF+ tumors, since SF+ and SF− cells exhibited similar in vitro proliferation kinetics. Since axillary nodal metastasis is also a function of primary tumor size, it is not certain the degree to which increased tumor cell invasiveness as opposed to increased primary tumor size were responsible for the higher rate of axillary nodal involvement of SF+ tumor cells.

The more rapid in vivo growth of SF+ tumors may be explained, in part, by an increase in the proportion of cycling cells (PCNA index), but the difference in the PCNA indices of SF+ vs SF− tumors was modest (70% vs 60%). The in vivo cell cycle times were not measured, which might have been shorter in the SF+ tumor group. Slower tumor growth or tumor stasis has been attributable to increased levels of apoptosis in some in vivo tumor models (Holmgren et al., *Nature Medicine* 1: 149–153 (1995)). The difference in in vivo growth rates of SF+ vs SF− tumors cannot be explained by differences in the rates of apoptosis, since both tumor types had equally low (ca. 1%) TdT labeling indices. Classic regions of necrosis were observed in both SF+ and SF− tumors, but there did not appear to be obvious differences in the degrees of necrosis either. However, several lines of evidence suggest that SF+ tumors had an enhanced angiogenic phenotype as compared with SF− tumors.

Microvessel density in highly angiogenic regions of human tumors was proposed as a standard measure of tumor angiogenesis and as a prognostic indicator (Weidner et al., *New Engl J Med* 324: 1–8 (1991), *JNCI* 84: 1875–1887 (1992)). Sections of SF+ tumors had higher microvessel densities than SF− tumors, whether the single highest MVC value was taken or the 3–4 highest values were averaged (P<0.001). Chemotactic activity for capillary endothelial cells is thought to be an in vitro correlate of angiogenesis (Tolsma et al., *J Cell Biol* 122: 497–511 (1993)). The inventors found that: (a) CM from SF+ cells and protein extracts from SF+ primary tumors had increased chemotactic activity for HDMECs as compared with CM and extracts from SF− cells and tumors; and (b) the chemotactic activity from SF+ cells and tumors was neutralized by an anti-SF monoclonal. SF+ tumor extracts also had more in vivo angiogenic activity in the rat corneal assay than did SF− tumor extracts; and the angiogenic activity from SF+ extracts was markedly inhibited by the anti-SF monoclonal. The observations that CM and extracts from SF+ tumors have increased chemotactic and angiogenic activity are consistent with the results from the microvessel counts. These findings suggest that higher levels of tumor angiogenesis contributed to the enhanced growth of SF+ tumors.

To determine if secondary alterations of other angiogenic regulators could have contributed to the observed results, the tumor contents of the angiogenic growth factor VEGF and the anti-angiogenic glycoprotein TSP1 were measured. The VEGF content was higher in SF− tumors than in SF+ tumors; and the VEGF titers were 100-fold lower than the SF titers in SF+ tumors. Thus, it is unlikely that alterations in VEGF expression contributed to increased tumor angiogenesis in SF+ tumors. TSP1 is a multidomain adhesive glycoprotein of the extracellular matrix with potent anti-angiogenic activity in vitro and in vivo (Good et al., *PNAS USA* 87: 6624–6628 (1990); Tolsma et al., *J Cell Biol* 122: 497–511 (1993)). Transfection of MDAMB435 human breast cancer cells with full-length TSP1 cDNA caused reduced growth of the primary tumor, reduced metastatic rate, and inhibition of angiogenesis (Weinstat-Saslow et al., *Cancer Res* 54: 6504–6511 (1994)). Assays of the TSP1 content of tumor extracts revealed that clone 29 SF+ tumors, the fastest growing of the four clones studied, had the lowest TSP1 content, while clone 32 tumors, the slowest growing, had the highest TSP1 content (P<0.001 for clone 29 vs 32). The net angiogenic phenotype of a tumor is likely to be determined by the balance between angiogenic and anti-angiogenic factors within the tumor. Thus, the finding of an inverse relationship between TSP1 content and tumor growth rate for clones 29 and 32 suggest that TSP1 may have influenced the angiogenic phenotype of these clones. However, SF+ clone 21 tumors grew more rapidly, showed higher MVCs, and contained more angiogenic activity than SF− clone 34 tumors, despite having similar TSP1 content. Therefore, it does not appear as if secondary alteration in tumoral TSP1 content was a major determinant of tumor growth or angiogenesis in this study.

The inventors' studies indicate that endogenous overexpression of SF stimulates growth of human breast cancer xenografts, but they do not by themselves establish a role for SF in malignant growth of breast cancer. Various other studies provide circumstantial evidence that SF contributes to breast cancer growth or progression. While none of 10 lines of human breast carcinoma cells produced SF in vitro (Yamashita et al., *Res Commun Chem Pathol Pharmacol* 82: 249–252 (1993); Rosen et al., *J Cell Biol* 127: 225–234 (1994)), both SF and c-met receptor were detected in vivo in carcinoma cells by in situ hybridization and immunostaining of human breast cancer tissue sections (Wang et al., *Science* 266: 117–119 (1994); Tuck et al., *Am J Pathol* 148: 225–232 (1996)). Thus, carcinoma cells may lose the ability to produce SF during in vitro passage, or the cells that give rise to mass cultures may be SF negative. Yamashita and colleagues (1994) measured the SF content of 258 primary invasive breast cancers and reported that high SF content is a powerful, independent predictor of relapse and death. The SF content of 167 primary breast cancers was measured and a much higher SF content was found in invasive vs ductal carcinoma-in-situ tumors and in primary tumors in which axillary lymph nodes were involved (Yao et al., in press). It was found that tumor SF content was strongly associated with tumor content of von Willebrand's factor, suggesting a correlation between SF content and tumor vascularity (34). The highest SF content values in human breast cancers (3–14 ng SF/mg protein) were less than the average values in SF+ xenografts (43 ng SF/mg protein). However, the minimum SF level needed to stimulate tumor growth is not known. In addition, human breast stroma (eg., endothelial cells) may be more sensitive to human SF than is mouse mammary fat pad stroma. Taken together with other studies, the findings set forth herein strengthen the case that SF contributes to human breast cancer growth.

Angiogenic regulatory factors have been found to modulate growth of human breast cancers in several other orthotopic xenograft models. As cited above, transfection of MDAMB435 cells with TSP1 inhibited tumor growth and angiogenesis (Weinstat-Saslow et al., *Cancer Res* 54: 6504–6511 (1994)). MCF-7 cells, which normally require estrogen supplementation for sustained in vivo tumor growth in nude mice, exhibited progressive estrogen-independent tumor growth when pro-angiogenic fibroblast growth factors (FGF-1 and FGF-4) were transfected into and overexpressed in the cells. These FGF-dependent tumors continued to grow, even in the presence of tamoxifen (Kern et al., *Breast Cancer Res Treat* 31: 153–165 (1994)). However, treatment of untransfected MCF-7 tumors with tamoxifen resulted in tumor regression and necrosis, which could be attributed, in part, to inhibition of angiogenesis and of endothelium growth (Haran et al., *Cancer Res* 54:

5511–5514 (1994)). Systemic administration of angiostatin, a fragment of plasminogen with strong anti-angiogenic activity, inhibited the growth of a subcutaneous human breast carcinoma primary tumor in SCID mice (O'Reilly et al., *Nature Med* 2: 689–692 (1996)). Angiostatin-treated tumors showed reduced angiogenesis and increased tumor cell apoptotic indices in the absence of any change in the tumor cell proliferative index.

In conclusion, transfection with SF cDNA induces increased growth of human breast cancer cells in the mammary fat pads of nude mice. The increased growth rate of SF+transfected tumors is due, in part, to increased tumor angiogenesis induced by SF.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method for promoting angiogenesis in a tissue comprising directly contacting said tissue with scatter factor in an amount effective to promote angiogenesis in said tissue.

2. The method of claim 1, wherein the tissue is selected from the group consisting of fibrous, endothelial, epithelial, vesicular, cardiac, cerebrovascular, muscular, vascular, transplanted, or wounded.

3. The method of claim 1, wherein the tissue is ischemic.

4. The method of claim 3, wherein the ischemic tissue is selected from the group consisting of myocardial ischemic tissue, cerebrovascular ischemic tissue, or veno-occlusive diseased tissue.

5. The method of claim 4, wherein the myocardial ischemic tissue is coronary artery disease.

* * * * *